US009744211B2

(12) United States Patent
Jiang

(10) Patent No.: US 9,744,211 B2

(45) Date of Patent: Aug. 29, 2017

(54) USES OF BT LIPOPEPTIDES AS THERAPEUTICS FOR OBESITY AND RELATED DISEASES

(71) Applicant: MYGALAXY LIMITED COMPANY, Fort Worth, TX (US)

(72) Inventor: Yiwei Jiang, Fort Worth, TX (US)

(73) Assignee: MYGALAXY Limited Company, Fort Worth, TX (US)

( * ) Notice: Subject to any disclaimer, the term of this patent is extended or adjusted under 35 U.S.C. 154(b) by 0 days.

(21) Appl. No.: 14/652,712

(22) PCT Filed: Dec. 17, 2013

(86) PCT No.: PCT/US2013/075521

§ 371 (c)(1),
(2) Date: Jun. 16, 2015

(87) PCT Pub. No.: WO2014/099829

PCT Pub. Date: Jun. 26, 2014

(65) Prior Publication Data

US 2016/0193287 A1 Jul. 7, 2016

Related U.S. Application Data

(60) Provisional application No. 61/738,166, filed on Dec. 17, 2012.

(51) Int. Cl.

| | |
|---|---|
| ***A61K 38/16*** | (2006.01) |
| ***A61K 38/10*** | (2006.01) |
| ***A61K 49/00*** | (2006.01) |
| ***G01N 33/50*** | (2006.01) |

(52) U.S. Cl.

CPC ............ *A61K 38/164* (2013.01); *A61K 38/10* (2013.01); *A61K 49/0008* (2013.01); *G01N 33/5023* (2013.01)

(58) Field of Classification Search

CPC ........ C12N 1/20; C12N 1/36; C12N 15/8286; C12N 15/8242; C12N 15/8243; C12N 15/8249; C12N 15/8266; C12N 9/0004; A61K 35/742; A61K 38/10; A61K 38/164; A61K 49/0008; C07K 14/345; C07K 14/325; C07K 7/08; C07K 14/195; C07K 2319/00

See application file for complete search history.

(56) References Cited

U.S. PATENT DOCUMENTS

| | | | |
|---|---|---|---|
| 2002/0035239 A1 | 3/2002 | Anderson et al. | |
| 2006/0228398 A1 | 10/2006 | Jiang | |
| 2008/0089883 A1 | 4/2008 | Kandimalla et al. | |
| 2012/0225037 A1 | 9/2012 | Jiang | |

FOREIGN PATENT DOCUMENTS

| | | |
|---|---|---|
| WO | WO2005074626 | 8/2005 |
| WO | WO 2012/090005 | 7/2012 |

OTHER PUBLICATIONS

Rubenstein AH. Trans. Amer. Clin. Climatolog. Assoc. 116: 103-113, 2005.*

Barsby et al., "Bogorol A produced in culture by a marine *Bacillus* sp. reveals a novel template for cationic peptide antibiotics," Org Lett, 2001, 3:437-440.

Barsby et al., "The Bogorol family of antibiotics: template-based structure elucidation and a new approach to positioning enantiomeric pairs of amino acids," J Org Chem, 2006, 71:6031-6037.

Jiang et al., "The efficacy of TAMUS 2032 in preventing a natural outbreak of colibacillosis in broiler chickens in floor pens," Poult Sci, 2005, 84:1857-1859.

Kogut et al., "The effects of the BT/TAMUS 2032 cationic peptides on innate immunity and susceptibility of young chickens to extraintestinal *Salmonella enterica* serovar Enteritidis infection," Int Immunopharmacol, 2007, 7:912-919.

Kogut et al., "BT cationic peptides: small peptides that modulate innate immune responses of chicken heterophils and monocytes," Vet Immunol Immunopathol, 2012, 145:151-158.

Kogut et al., "Feeding the BT Cationic Peptides to Chickens at Hatch Reduces Cecal Colonization by *Salmonella enterica* Serovar Enteritidis and Primes Innate Immune Cell Functional Activity," Foodborne Pathog Dis., 2009 7(1):23-30.

Wu et al., "Structure and biosynthesis of the BT peptide antibiotic from Brevibacillus texasporus," Appl Environ Microbiol, 2005, 71:8519-8530.

Eckel et al., "Obesity and type 2 diabetes: what can be unified and what needs to be individualized?" Diabetes Care., 34(6):1424-30, Epub May 20, 2011.

Greenway, "Obesity medications and the treatment of type 2 diabetes," Diabetes Technol Ther., 1(3):277-287, Fall 1999.

European search report for EP13866071.7, dated Sep. 7, 2016, 9 pages.

* cited by examiner

*Primary Examiner* — S. Devi

(74) *Attorney, Agent, or Firm* — Fish & Richardson P.C.

(57) ABSTRACT

The invention provides compositions and uses for treating or preventing obesity and related diseases in patients.

6 Claims, 6 Drawing Sheets

SEQUENCE LISTING

```
<160> NUMBER OF SEQ ID NOS: 21

<210> SEQ ID NO 1
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 1

Xaa Xaa Leu Xaa Ile Val Val Lys Val Leu Lys Tyr Leu Xaa
1               5                   10


<210> SEQ ID NO 2
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
```

-continued

<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 2

```
Xaa Xaa Met Xaa Ile Val Val Lys Val Leu Lys Tyr Leu Xaa
1               5                   10
```

<210> SEQ ID NO 3
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 3

```
Xaa Xaa Val Xaa Ile Val Val Lys Val Leu Lys Tyr Leu Xaa
1               5                   10
```

<210> SEQ ID NO 4
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 4

```
Xaa Xaa Leu Xaa Ile Ile Val Lys Val Leu Lys Tyr Leu Xaa
1               5                   10
```

<210> SEQ ID NO 5
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (14)..(14)
<223> OTHER INFORMATION: valinol

<400> SEQUENCE: 5

Xaa Xaa Leu Lys Ile Ile Val Lys Val Leu Lys Tyr Leu Xaa
1 5 10

<210> SEQ ID NO 6
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 6

Xaa Xaa Val Xaa Val Val Val Lys Val Leu Lys Tyr Leu Xaa
1 5 10

<210> SEQ ID NO 7
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 7

Xaa Xaa Met Xaa Ile Ile Val Lys Val Leu Lys Tyr Leu Xaa
1 5 10

-continued

<210> SEQ ID NO 8
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 8

Xaa Xaa Ile Xaa Ile Val Val Lys Val Leu Lys Tyr Leu Xaa
1 5 10

<210> SEQ ID NO 9
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 9

Xaa Xaa Phe Xaa Ile Val Val Lys Val Leu Lys Tyr Leu Xaa
1 5 10

<210> SEQ ID NO 10
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)

<223> OTHER INFORMATION: valinol

<400> SEQUENCE: 10

Xaa Xaa Leu Xaa Ile Leu Val Lys Val Leu Lys Tyr Leu Xaa
1 5 10

<210> SEQ ID NO 11
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 11

Xaa Xaa Met Xaa Ile Leu Val Lys Val Leu Lys Tyr Leu Xaa
1 5 10

<210> SEQ ID NO 12
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 12

Xaa Xaa Val Xaa Ile Ile Val Lys Val Leu Lys Tyr Leu Xaa
1 5 10

<210> SEQ ID NO 13
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)

<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 13

Xaa Xaa Val Xaa Ile Leu Val Lys Val Leu Lys Tyr Leu Xaa
1 5 10

<210> SEQ ID NO 14
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 14

Xaa Xaa Ile Xaa Ile Ile Val Lys Val Leu Lys Tyr Leu Xaa
1 5 10

<210> SEQ ID NO 15
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 15

Xaa Xaa Ile Xaa Ile Leu Val Lys Val Leu Lys Tyr Leu Xaa
1 5 10

<210> SEQ ID NO 16
<211> LENGTH: 14
<212> TYPE: PRT
<213> ORGANISM: Artificial Sequence
<220> FEATURE:

-continued

<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 16

```
Xaa Xaa Phe Xaa Ile Ile Val Lys Val Leu Lys Tyr Leu Xaa
1               5                   10
```

<210> SEQ ID NO 17
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 17

```
Xaa Xaa Phe Xaa Ile Leu Val Lys Val Leu Lys Tyr Leu Xaa
1               5                   10
```

<210> SEQ ID NO 18
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 18

```
Xaa Xaa Leu Xaa Val Val Val Lys Val Leu Lys Tyr Leu Xaa
```

1 5 10

<210> SEQ ID NO 19
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 19

Xaa Xaa Met Xaa Val Val Val Lys Val Leu Lys Tyr Leu Xaa
1 5 10

<210> SEQ ID NO 20
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine
<220> FEATURE:
<221> NAME/KEY: MISC_FEATURE
<222> LOCATION: (14)..(14)
<223> OTHER INFORMATION: valinol

<400> SEQUENCE: 20

Xaa Xaa Ile Xaa Val Val Val Lys Val Leu Lys Tyr Leu Xaa
1 5 10

<210> SEQ ID NO 21
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: 2-hydroxy-3-methylpentanoic acid
<220> FEATURE:
<221> NAME/KEY: MISC_FEATURE
<222> LOCATION: (2)..(2)
<223> OTHER INFORMATION: 2,3-dehydro-2-aminobutyric acid
<220> FEATURE:
<221> NAME/KEY: MISC_FEATURE
<222> LOCATION: (4)..(4)
<223> OTHER INFORMATION: ornithine -continued

```
<220> FEATURE:
<221> NAME/KEY: MISC_FEATURE
<222> LOCATION: (14)..(14)
<223> OTHER INFORMATION: valinol

<400> SEQUENCE: 21

Xaa Xaa Phe Xaa Val Val Val Lys Val Leu Lys Tyr Leu Xaa
1               5                   10
```

USES OF BT LIPOPEPTIDES AS THERAPEUTICS FOR OBESITY AND RELATED DISEASES

CROSS REFERENCE TO RELATED APPLICATIONS

This application is a National Stage Application under 35 U.S.C. §371 and claims the benefit of International Application No. PCT/US2013/075521, filed Dec. 17, 2013, which claims the benefit of U.S. Provisional Application No. 61/738,166, filed Dec. 17, 2012, the entirety of which are incorporated by reference.

TECHNICAL FIELD

The present invention relates in general to the field of biotechnology, more specifically, to use of a family of lipopeptides to treat or prevent obesity and obesity-related diseases including type 2 diabetes mellitus.

BACKGROUND

Obesity causes a group of serious diseases collectively known as metabolic syndrome. These obesity-related diseases include insulin resistance (type 2 diabetes mellitus), atherogenic dyslipidemia (leading to cardiovascular diseases), hypertension (risking stroke, heart attacks and chronic kidney failure) and fatty liver. A strong association between type 2 diabetes mellitus and obesity has helped coin the term “diabesity”. Obesity is one of the most critical and widespread health issues, affecting more than 400 million people worldwide. Rates of obesity in developing countries have tripled in the last 20 years, while American obesity rates are the highest in the world. 64 percent of United States adults are overweight or obese, and about one-third of American children and adolescents are overweight or obese. There is no shortage of “treatments” for obesity, including prescription and over-the-counter medications, weight loss programs, diets and exercise regimens. Some of these solutions work, but they almost categorically result in unmet expectations for both doctors and patients, with no long-term improvement in weight or overall health. The few prescription medications currently available work to centrally suppress appetite or to block fat absorption (as anti-nutrients). However, these therapies suffer from limited efficacy and/or various adverse effects. Most patients on these therapies rebound and continue to gain weight.

Obesity is not just the result of imbalanced energy intake over expenditure. Besides host genetics, diet and exercise, the gut microbiota has emerged as a key environmental factor in the development of obesity and metabolic syndrome (i.e. in genetically obese ob/ob mice) with changes of the gut microbiota in the relative abundance of the two dominant bacterial divisions (the Bacteroidetes and the Firmicutes) (Ley et al., 2005) and an increased capacity to harvest energy from the diet. The obesity trait is also transmissible or infectious: colonization of germ-free mice with an “obese microbiota” results in a significantly greater increase in total body fat than colonization with a “lean microbiota” (Turnbaugh et al., 2006), while germ-free mice are resistant to high-fat-induced diabesity (Backhed et al., 2004; Backhed et al., 2007; Rabot et al., 2010). More importantly, lipopolysaccharide (LPS) produced by Gram-negative bacteria of the gut microbiota plays a triggering role in diabesity via “metabolic endotoxemia”:high-fat diet increases not only the proportion of LPS-containing bacteria but also intestinal permeability for LPS (Cani et al., 2007). Accordingly, known microbiota modulators/gut barrier enhancers which confer general health benefits to the host animal, such as probiotics (Lee et al., 2006; Ma et al., 2008; Aronsson et al., 2010; Kadooka et al., 2010; Kang et al., 2010; Kondo et al., 2010; Chen et al., 2011; Delzenne et al., 2011; Mozaffarian et al., 2011; Fak and Backhed, 2012; Ji et al., 2012; Teixeira et al., 2012) and prebiotics (Keenan et al., 2006; Zhou et al., 2008; Zhou et al., 2009), have showed promise as new clinical tools in this specific therapeutic area of obesity and metabolic syndrome, though issues such as dietary changes undesirable to humans (i.e. >8% resistant starch prebiotic in diet) may limit the usefulness of these methods. However, in keeping with the long-held concept of intestinal immune tolerance and undermining a previous theory from (Vijay-Kumar et al., 2010), (Ubeda et al., 2012) have recently found that the anti-infective innate immunity controlled by the pathogen-pattern-sensing toll-like receptors (TLRs) seems unable to overcome the tolerance to target the obesogenic symbiotic commensal microbes in an “obese microbiota” as foreign infectious pathogens and induce a leanogenic microbiota to prevent obesity and metabolic syndrome, depriving the basis for speculating an anti-diabesity use of an anti-infective innate immunomodulator.

Currently, the only approved effective treatment for obesity is Gastric Bypass Surgery. In normal digestion, food passes through the stomach and enters the small intestine, where most of the nutrients and calories are absorbed; it then passes into the large intestine (colon), and the remaining waste is eventually excreted. In a prototypical Roux-en-Y Gastric Bypass, the stomach is made smaller by creating a small pouch at the top of the stomach using surgical staples or a plastic band; the smaller stomach is connected directly to the middle portion of the small intestine (jejunum), bypassing the rest of the stomach and the upper portion of the small intestine (duodenum). In addition to appetite suppression and a typical weight loss of 20 to 30 kg, which can be maintained for up to 10 years (Maggard et al., 2005), Gastric Bypass completely resolves type 2 diabetes mellitus within days after the surgery and well before significant weight loss. However, Gastric Bypass Surgery is restricted to the extremely obsessed due to high surgical cost, a significant mortality rate due to complications at about 1%, a failure rate at about 15%, irreversibility, gallstones, malabsorption-caused lean mass loss and a requirement of nutritional supplementation. The underlying anti-diabesity mechanism for Gastric Bypass is believed to be diverting undigested nutrients to the mid- and lower-GI track to stimulate secretion of appetite-suppressing anti-diabesity GI peptide hormones such as peptide YY (PYY), glucagon-like peptide-1 (GLP-1), oxyntomodulin (OXM) and cholecystokinin (CCK) by nutrient-sensing enteroendocrine cells (Geraedts et al., 2009; Geraedts et al., 2010; Laferrere et al., 2010; Peterli et al., 2012). Attempts to use these anti-diabesity hormones as injectable mono-therapeutics to treat obesity have been unsuccessful likely due to a need to simultaneously administer more than one hormone (Field et al., 2010). Interestingly, oral taste receptor cells display great functional similarities (in receptor expression and GI hormone production) to GI enteroendcrine cells (Wu et al., 2002; Dyer et al., 2005; Bogunovic et al., 2007; Palazzo et al., 2007; Wang et al., 2009), and (Acosta et al., 2011) showed that PYY delivered to the oral cavity of DIO mice induced fairly good reductions of food intake and body weight likely via interaction with the specific Y2 receptor on the fibers of afferent taste nerves in oral mucosa (also see U.S. Ser. No. 13/145,660). So far there are no known agents or methods capable of stimulating production of multiple GI hormones in the oral taste receptor cells to confer anti-diabesity effects.

The Gastric Bypass Surgery and (adverse effect-prone) anti-nutrient strategies have significant mechanistic overlap in up-regulating GI hormones, as anti-nutrients (such as dirlotapide) inhibit nutrient absorption to induce secretion of GI hormones (Wren et al., 2007).

The Gastric Bypass Surgery and the microbiota modulation/gut barrier enhancement anti-diabesity therapeutics (prebiotics and probiotics) also have significant mechanistic overlap in up-regulation of the GI hormones. Colonic fermentation of the anti-diabesity prebiotic, non-digestible resistant starch, liberates short-chain fatty acids to cause day-long sustained secretion of PYY and GLP-1 (Keenan et al., 2006; Zhou et al., 2008; Zhou et al., 2009). TLR agonists such as the TLR2 agonist lipoprotein/lipopeptide (Sturm et al., 2005), the TLR5 agonist flagellin (Schlee et al., 2007; Troge et al., 2012) and the TLR9 agonist CpG DNA (Lammers et al., 2003; Menard et al., 2010; Zhong et al., 2012) are important contributory factors to the beneficial effects of a probiotic. TLR agonists also have non-immunomodulatory functions of directly inducing the enteroendocrine secretion of GI hormones (which have no reported activities to enhance anti-infective innate immunity against pathogen challenges). Enteroendocrine cells such as the STC-1 cells express functional TLRs including TLR2 (Bogunovic et al., 2007). Activation of TLR4, TLR5 or TLR9 (with respective agonist LPS, flagellin or CpG oligo DNA) induces the secretion of the GI hormone CCK from STC-1 enteroendocrine cells as well as in C57BL/6 mice (Palazzo et al., 2007), implying a TLR-mediated anti-diabesity enteroendocrine mechanism for probiotics. In addition, saturated fatty acids are agonists for both TLR4 and TLR2 (Lee et al., 2001; Lee et al., 2004), thus these two TLRs may play direct nutrient-sensing roles for the most diabeisty-relevant nutrients in enteroendocrine cells. However, the potential of this immunity-independent TLR-GI hormone pathway remains unexploited in the absence of a novel non-absorbable noninflammatory TLR agonist, because the above traditional inflammatory TLR agonists have to be excluded from the use as an anti-diabesity agent to prevent a potentially harmful TLR-mediated systemic inflammatory response (as mentioned above, LPS can actually induce metabolic syndrome). Therefore, there is the need in the art of novel therapeutics for obesity and metabolic syndrome.

*Brevibacillus texasporus* (e.g., ATCC PTA-5854) is a previously identified soil bacterium that expresses a non-ribosomal peptide synthetase (NRPS, encoded by the operon under GenBank accession number AY953371) to produce a family/mixture of related cationic NRP variants of 13 amino acid residues ("BT peptides" or "BT lipopeptides" in light of their newly resolved N-terminal structure, and the two terms are interchangeable in the present disclosure), among which BT1583 is the most abundant variant (WO/2005/074626). The cationic peptides (as a mixture or individual peptides isolated from *B. texasporus*) display a broad-spectrum antibacterial activity in vitro (BT Function #1). The high degree of 16S rDNA sequence identity (98.5%) between PTA-5854 and the *Brevibacillus laterosporus* type strain classifies *Brevibacillus texasporus* as a subspecies of *Brevibacillus laterosporus*, with *Brevibacillus laterosporus* subsp. texasporus defined as *Brevibacillus laterosporus* strains that produce the nonribosomal peptides from the BT NRPS (or BT peptides). Genomic sequencing of at least two *B. laterosporus* strains (LMG 15441 and GI-9) has validated this taxonomy. Both genomes (published respectively under GenBank accession number AFRV00000000 and EMBL accession numbers CAGD01000001 to CAGD01000061) contain an intact BT NRPS operon with 99% DNA sequence identity to AY953371, even though these *B. laterosporus* strains are not known to be producers of BT peptides. "*Brevibacillus texasporus*", "*Brevibacillus laterosporus* subsp. *texasporus*" and "*B. texasporus*" are thus synonymous.

The exact identity of the N-terminal residue (including its modification) of the BT peptides was unknown, and WO/2005/074626 provided a tentative N-terminal assignment of a doubly methylated Bmt, (4R)-4-[(E)-2-butenyl]-4-methyl-L-threonine and an overall BT1583 structure of $Me_2$-Bmt-Leu-$_D$Orn-Ile-Val-Val-$_D$Lys-Val-$_D$Leu-Lys-$_D$Tyr-Leu-Vol, in which Orn stands for ornithine and Vol stands for valinol. Though BT peptides were discovered as antibiotics based on their antibacterial activities in vitro, (WO/2005/074626 and (Wu et al., 2005)), orally delivered BT peptides (as a mixture isolated from *B. texasporus*) lack antibacterial activity in vivo. For example, vancomycin-resistant enterococci (VRE) are highly sensitive to the BT peptides in vitro, but orally delivered BT peptides at concentrations well above the minimal inhibition concentration fail to decolonize VRE in the mouse GI track (Kogut et al., 2007). Importantly, orally delivered BT peptides are neither digested nor absorbed in the GI track, likely due to the presence of D-form amino acid residues and their relative highly molecular weights at about 1,600 daltons respectively. Nevertheless, orally delivered BT peptides (also as a mixture isolated from *B. texasporus*) can cause a number of beneficial systemic effects to animals. Orally delivered BT peptides are effective in preventing respiratory colibacillosis (air sac *E. coli* infection) and promoting growth and increasing feed conversion in young chickens (Jiang et al., 2005). Perhaps more importantly, the in vivo anti-infective effects of BT peptides appear to be independent of the in vitro antibiotic activities, as orally delivered BT peptides are effective in preventing infections in chickens by *E. coli* and *Salmonella* at concentrations below the in vitro minimal inhibition concentrations (Jiang et al., 2005; Kogut et al., 2007; Kogut et al., 2009). It is also discovered that circulating heterophils and monocytes are primed (rather than activated) in BT-fed chickens, pointing to innate immunity modulation as a likely mechanism of action for these in vivo anti-infective effects. Considering the fact that orally delivered BT peptides travel through the GI track without being digested or absorbed, BT peptides may stimulate intestinal epithelial cells to secret factors into the blood which in turn prime leukocytes to enhance anti-infective immunity (BT Function #2).

Bogorols are a family of 5 lipopeptide antibiotics isolated from a marine bacterium *Brevibacillus laterosporus* PNG276 found in a Papua New Guinea tubeworm (U.S. Pat. No. 6,784,283), which also produces a number of other antibiotics, including the lipopeptide antibiotic Tauramamide (Gerard et al., 1999; Desjardine et al., 2007). The most abundant variant bogorol A has a reported molecular weight of 1,584 and a reported structure (SEQ ID No: 1) of Hmp-$_E$Dhb-Leu-$_D$Orn-Ile-Val-Val-$_D$Lys-Val-$_D$Leu-Lys-$_D$Tyr-Leu-Vol, in which Hmp stands for 2-hydroxy-3-methylpentanoic acid and Dhb stands for 2,3-dehydro-2-aminobutyric acid (Barsby et al., 2001; Barsby et al., 2006). As a prelude to the present invention, the inventor discovered that BT peptides are lipopeptides: BT1583 has the same structure as bogorol A, the BT and bogorol families share four common NRP members, and thus *Brevibacillus laterosporus* PNG276 is also a *B. texasporus strain* (Examples 1 and 2).

SUMMARY OF THE INVENTION

The present invention is based partly on inventor's discovery that protease-resistant BT peptides are capable of inducing physiological changes typically mediated by nutrient-sensing enteroendocrine/taste receptor cells, therefore can be used as an oral anti-diabesity pseudo-nutrient (BT Function #3). Orally delivered BT peptides are shown to completely reverse diet-induced and genetic obesity and insulin resistance in a pattern consistent with body weight normalization rather than unidirectional weight loss.

In one aspect, the present invention provides a pharmaceutical composition for treating or preventing obesity and diseases related to obesity, comprising of an effective amount of one or more BT lipopeptides. For example, the BT lipopeptide of the present invention has the sequence selected from SEQ ID NOS: 1 to 21. BT lipopeptides can be made naturally using a *B. texasporus* strain (as a mixture or further purified individual peptides) or via chemical synthesis. BT lipopeptides of this invention are provided as isolated water-soluble peptides, i.e. in a substantially purified form. A "substantially purified form" is one wherein one or more peptides of this invention constitute at least about 1 weight percent of a composition, preferably at least about 10 weight percent, more preferably at least about 25 weight percent, still more preferably at least about 50 weight percent, yet still more preferably at least about 75 weight percent, and yet still more preferably at least about 95 weight percent, and most preferably at least about 99 weight percent. In one embodiment, a pharmaceutical composition of the invention may comprise an effective amount of BT peptides as a mixture isolated from *B. texasporus*. Peptides of this invention may be provided as salts, which salts include acid or base addition salts, depending on whether the moiety on the peptide (e.g. an amino acid side group) being connected to a salt is a basic or acidic moiety. Preferably, the salt will be acceptable for pharmaceutical purposes. This invention also provides peptides of this invention and pharmaceutically acceptable salts thereof, in a pharmaceutical composition. A pharmaceutical composition of the invention may not necessarily contain a BT peptide or peptides of this invention in a substantially purified form because the composition may contain carriers, diluents, or other materials suitable for use in pharmaceutical compositions, in admixture with the peptide(s).

In one embodiment, the pharmaceutical composition of the present invention for treating or preventing obesity and diseases related to obesity is an oral dose form that comprises an effective amount of water-soluble BT lipopeptides and ingredients that promote the peptides' contact with and/or exposure to the oral cavity of a subject. In a specific embodiment, the oral dose form is an aqueous solution comprising one or more BT lipopeptides.

In another embodiment, the invention pertains to a method of inducing satiation in a subject that includes applying to at least a portion of the mouth of the subject a composition comprising one or more BT lipopeptides in a water-soluble form at a time period prior to eating (preprandial). The time period may be 5 seconds or more. In a specific embodiment, the time period is 5-360 min prior to eating. In a more specific embodiment, the time period is 30-120 min prior to eating.

Another embodiment relates to a container comprising a solid (e.g. powder), fluid or semi-fluid composition that comprises one or more BT lipopeptides in a water-soluble form and a pharmaceutically acceptable carrier. In a specific embodiment the container comprises a nozzle for ejecting the composition into the mouth of a subject. The container may be under pressure and/or be equipped with a pump nozzle.

Another embodiment relates to a mouth applicable article loaded with one or more BT lipopeptides in a water-soluble form. The article may be a chewing gum loaded with one or more BT lipopeptides; a lozenge (eg a dissolvable solid or semi-solid object intended to hold in the mouth for a period of time) loaded with one or more BT lipopeptides, or a permeable pouch or sponge loaded with one or more BT lipopeptides. The article is designed for extended delivery of one or more BT lipopeptides to the mouth and/or pharynx, as opposed to conventional oral administration that involves the immediate swallowing of a pill, tablet or capsule composition as is conventionally understood as oral administration. In particular, the article is designed for delivery to the tongue.

In a specific embodiment, one or more BT lipopeptides is delivered to the mouth and/or pharynx of a subject according to a generally continuous time period of at least 5, 10, 15 or more seconds. In another embodiment, the delivery is for 0.1-120 minutes, including any specific 0.1 minute increment within such range.

In certain embodiments, a formulation is prepared for spraying into the mouth. The pharmaceutical composition may be placed in a container equipped with a sprayer nozzle and either ejected through a pump motion or by release of pressure.

In another embodiment, the pharmaceutical composition is combined and provided in the form of a chewing gum.

In another aspect, the present invention provides a method of treating or preventing obesity and obesity-related diseases by orally administering an effective amount of one or more BT lipopeptides. One exemplary embodiment of the invention comprises selecting an obese or overweight patient, orally administering to the patient an amount of one or more BT lipopeptides effective to reduce body weight or body weight gain. Another exemplary embodiment of then invention is a method of treating or preventing type 2 diabetes mellitus, comprising orally administering to the patient an amount of one or more BT lipopeptides effective to control the blood glucose level and increase insulin sensitivity. Another embodiment of the invention is a method of treating or preventing combined hyperlipidemia, comprising orally administering to the patient an amount of one or more BT lipopeptides effective to control blood LDL cholesterol and triglyceride levels. Another exemplary embodiment of the invention is a method of treating or preventing non-alcoholic fatty liver, comprising orally administering to the patient an amount of one or more BT lipopeptides effective to treat or prevent fat accumulation in liver and subsequent liver failure. Yet another exemplary embodiment of the invention is a method of treating or preventing hypertension, comprising orally administering to the patient an amount of one or more BT lipopeptides effective to treat or prevent high blood pressure.

In one more aspect, this present invention provides a method of reducing food intake, comprising selecting an obese or overweight patient, orally administering to the patient an amount of one or more BT lipopeptides effective to reduce food intake.

Preferably, the patient in the present invention is a human patient.

The dosing level of the BT lipopeptides as a non-absorbable pseudo-nutrient according to the present invention is to be measured in mg of BT lipopeptides per kg of the dry weight of the food consumption per day (as opposed to mg per kg of body weight per day). The present invention provides that an effective amount of BT lipopeptide pseudo-nutrient is in the range between 100 to 10,000 mg per kg of the dry weight of the food consumption per day in a single or divided dose.

Also provided in the present invention is a method to identify new oral anti-diabesity agent, comprising identifying a noninflammatory TLR agonist via screening in vitro with innate immunity cells and then testing for indigestibility, non-absorption and anti-diabesity effects in a diabesity animal model (i.e. DIO, db/db or ob/ob mice) via oral delivery. The present invention also provides a method of treating obesity and obesity-related diseases using such new oral anti-diabesity agent.

Furthermore, the present invention provides BT lipopeptides as an oral adjuvant to enhance the immune response to a vaccine, such as a vaccine against microbial (*Mycobacterium tuberculosis, Escherichia coli, Salmonella, Campylobacter. Staphylococcus aureus, Enterococcus faecium, Streptococcus pneumoniae*, gonorrhea, *Pseudomonas aeruginosa, Clostridium difficile, Acinetobacter baumannii*, HIV, influenza, HBV, HCV, Herpes viruses, Filoviruses, Epstein-Barr virus, HPV, Kaposi's sarcoma-associated herpesvirus, Human T-lymphotropic viruses), parasitical infections, cancers and combinations thereof.

DETAILED DESCRIPTION OF THE INVENTION

Figure 1:
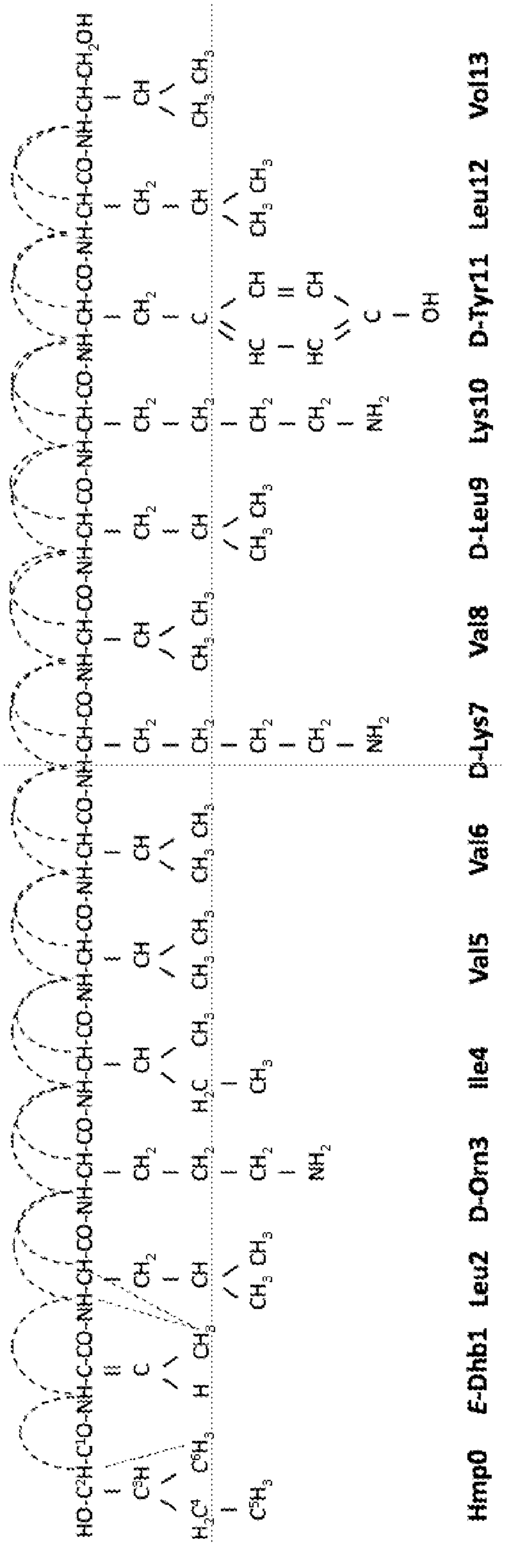
FIG. 1. Corrected structure of BT1583 with dash lines representing the $^1H$-$^1H$ NOEs FIG. 2. Oral BT treatment via in drinking water at 40 ppm caused no difference in weight gain, food or water intake in DIO mice FIG. 3. Oral glucose tolerance (oGTT) and glucose-induced insulin secretion in DIO mice were not changed by 30 days of oral BT treatment via drinking water at 40 ppm FIG. 4. Oral BT treatment via in drinking water at 400 ppm significantly reduced body weight, food and water intakes in DIO mice FIG. 5. Oral glucose tolerance (oGTT) and glucose-induced insulin secretion in DIO mice were significantly improved by 30 days of oral BT treatment via drinking water at 400 ppm FIG. 6. Body composition and hydration were significantly improved in the DIO mice by 30 days of oral BT treatment via drinking water at 400 ppm

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"NRP variants" refers to non-ribosomal peptides produced by a microorganism from the same NRPS. NRP variants may differ from one another in amino acid sequence by one or more residues depending on the extent of NRPS codon degeneracy in the NRPS.

"Noninflammatory TLR agonist" refers to a TLR agonist that cannot trigger a response in an innate immunity cell on its own but can increase the cell's response triggered by a separate stimulant. In other words, unlike traditional inflammatory TLR agonists (such as the TLR4 agonist LPS) which directly trigger an inflammatory response, the effect of a noninflammatory TLR agonist is priming-only.

"Pseudo-nutrients" refers to non-digestible and non-absorbable natural or synthetic compounds that can induce physiological changes typically mediated by nutrient-sensing enteroendocrine/taste receptor cells, such as secretion of GI hormones, anti-diabesity effects and enhanced nutrient absorption. Pseudo-nutrients are distinct from antinutrients (such as dirlotapide) which are natural or synthetic compounds that interfere with the absorption of nutrients to induce secretion of GI hormones (Wren et al., 2007).

The pathway of immunity-independent but TLR-mediated nutrient-sensing in enteroendocrine cells allows an efficient two-step strategy to identify new pseudo-nutrients which can induce secretion of anti-diabesity GI hormones from enteroendocrine/taste receptor cells. The first step involves identifying a noninflammatory (priming-but-not-activating) TLR agonist via screening compounds in vitro with innate immunity cells such as isolated leukacytes. The second step involves testing the TLR agonists for indigestibility, non-absorption and anti-diabesity effects in DIO, db/db or ob/ob mice via oral delivery of the TLR agonist. To avoid potentially harmful systemic inflammation, it is essential to exclude inflammatory TLR agonists such as LPS. The discovery of BT lipopeptide pseudo-nutrient provided the proof-of-concept for this screening strategy.

"Body Mass Index" (BMI) is a number based on a person's weight and height that provides a way to estimate the effect of weight on health. A person's weight in kilograms and height in meters: BMI=kilograms divided by (meters squared). A healthy "normal body weight" refers to a BMI is between 19 and 24.9. "Overweight" refers to a BMI between 25 and 29.9. "Obese" refers to a BMI 30 or higher.

"Administering" includes self-administering. "Oral delivery" or "oral administering" includes delivery or administering to and/or through oral cavity.

The BT peptides or BT lipopeptides used in the studies of Examples 3 though 7 were a mixture of natural BT NRP variants (including SEQ ID NOs: 1-9) isolated from *B. texasporus* using the isolation and detection methods disclosed in WO/2005/074626 and (Wu et al., 2005) but without the reverse-phase HPLC step to resolve the BT NRP variants. People skilled in the art can readily make the BT peptide or BT lipopeptides using the methods described in those references. The BT peptides or BT lipopeptides were characterized, and the amino acid sequences were provided below in Table 1. Table 1 describes the structures of the nine (above-detection-level) BT NRP variants and their typical relative abundances in such mixture (in which no non-BT-NRPS-originated peptides could be detected with mass spectrometry).

TABLE 1

Summary of BT NRP variants

| BT Variant | Peptide sequence | % | SEQ ID NO. | Bogo -rol |
|---|---|---|---|---|
| Dominant Variant | | | | |
| BT1583 | HmP-$_{E}$phb-Leu-$_{D}$Orn-Ile-Val-Val-$_{D}$Lys-Val-$_{D}$Leu-Lys-$_{D}$Tyr-Leu-Vol | 31 | 1 | A |
| Minor Variants | | | | |
| BT1601-M2 | Hmp-$_{E}$Dhb-***Met***-$_{D}$Orn-Ile-Val-Val-$_{D}$Lys-Val-$_{D}$Leu-Lys-$_{D}$Tyr-Leu-Vol | 26 | 2 | D |
| BT1569-V2 | Hmp-$_{E}$Dhb-***Val***-$_{D}$Orn-Ile-Val-Val-$_{D}$Lys-Val-$_{D}$Leu-Lys-$_{D}$Tyr-Leu-Vol | 20 | 3 | B |
| Detectable Variants | | | | |
| BT1597-I5 | Hmp-$_{E}$Dhb-Leu-$_{D}$Orn-Ile-***Ile***-Val-$_{D}$Lys-Val-$_{D}$Leu-Lys-$_{D}$Tyr-Leu-Vol | 6 | 4 | |
| BT1611-K3I5 | Hmp-$_{E}$Dhb-Leu-$_{D}$***Lys***-Ile-***Ile***-Val-$_{D}$Lys-Val-$_{D}$Leu-Lys-$_{D}$Tyr-Leu-Vol | 6 | 5 | |
| BT1555-V2V4 | Hmp-$_{E}$Dhb-***Val***-$_{D}$Orn-***Val***-Val-Val-$_{D}$Lys-Val-$_{D}$Leu-Lys-$_{D}$Tyr-Leu-Vol | 5 | 6 | C |
| BT1615-M2I5 | Hmp-$_{E}$Dhb-***Met***-$_{D}$Orn-Ile-***Ile***-Val-$_{D}$Lys-Val-$_{D}$Leu-Lys-$_{D}$Tyr-Leu-Vol | 4 | 7 | |
| BT1583-I2 | Hmp-$_{E}$Dhb-***Ile***-$_{D}$Orn-Ile-Val-Val-$_{D}$Lys-Val-$_{D}$Leu-Lys-$_{D}$Tyr-Leu-Vol | 1 | 8 | |
| BT1617-F2 | Hmp-$_{E}$Dhb-***Phe***-$_{D}$Orn-Ile-Val-Val-$_{D}$Lys-Val-$_{D}$Leu-Lys-$_{D}$Tyr-Leu-Vol | 1 | 9 | |
| Predicted Variants | | | | |
| BT1597-L5 | Hmp-$_{E}$Dhb-Leu-$_{D}$Orn-Ile-***Leu***-Val-$_{D}$Lys-Val-$_{D}$Leu-Lys-$_{D}$Tyr-Leu-Vol | | 10 | |
| BT1615-M2L5 | Hmp-$_{E}$Dhb-***Met***-$_{D}$Orn-Ile-***Leu***-Val-$_{D}$Lys-Val-$_{D}$Leu-Lys-$_{D}$Tyr-Leu-Vol | | 11 | |
| BT1583-V215 | Hmp-$_{E}$Dhb-***Val***-$_{D}$Orn-Ile-***Ile***-Val-$_{D}$Lys-Val-$_{D}$Leu-Lys-$_{D}$Tyr-Leu-Vol | | 12 | |
| BT1583-V2L5 | Hmp-$_{E}$Dhb-***Val***-$_{D}$Orn-Ile-***Leu***-Val-$_{D}$Lys-Val-$_{D}$Leu-Lys-$_{D}$Tyr-Leu-Vol | | 13 | |
| BT1597-I215 | Hmp-$_{E}$Dhb-***Ile***-$_{D}$Orn-Ile-***Ile***-Val-$_{D}$Lys-Val-$_{D}$Leu-Lys-$_{D}$Tyr-Leu-Vol | | 14 | |
| BT1597-I2L5 | Hmp-$_{E}$Dhb-***Ile***-$_{D}$Orn-Ile-***Leu***-Val-$_{D}$Lys-Val-$_{D}$Leu-Lys-$_{D}$Tyr-Leu-Vol | | 15 | |
| BT1631-F2I5 | Hmp-$_{E}$Dhb-***Phe***-$_{D}$Orn-Ile-***Ile***-Val-$_{D}$Lys-Val-$_{D}$Leu-Lys-$_{D}$Tyr-Leu-Vol | | 16 | |
| BT1631-F2L5 | Hmp-$_{E}$Dhb-***Phe***-$_{D}$Orn-Ile-***Leu***-Val-$_{D}$Lys-Val-$_{D}$Leu-Lys-$_{D}$Tyr-Leu-Vol | | 17 | |
| BT1569-V4 | Hmp-$_{E}$Dhb-Leu-$_{D}$Orn-***Val***-Val-Val-$_{D}$Lys-Val-$_{D}$Leu-Lys-$_{D}$Tyr-Leu-Vol | | 18 | |
| BT1587-M2V4 | Hmp-$_{E}$Dhb-***Met***-$_{D}$Orn-***Val***-Val-Val-$_{D}$Lys-Val-$_{D}$Leu-Lys-$_{D}$Tyr-Leu-Vol | | 19 | |
| BT1569-I2V4 | Hmp-$_{E}$Dhb-***Ile***-$_{D}$Orn-***Val***-Val-Val-$_{D}$Lys-Val-$_{D}$Leu-Lys-$_{D}$Tyr-Leu-Vol | | 20 | |
| BT1603-F2V4 | Hmp-$_{E}$Dhb-***Phe***-$_{D}$Orn-***Val***-Val-Val-$_{D}$Lys-Val-$_{D}$Leu-Lys-$_{D}$Tyr-Leu-Vol | | 21 | |

(Hmp stands for 2-hydroxy-3-methylpentanoic acid,
Dhb stands for 2,3-dehydro-2-aminobutyric acid which is synonymous with dehydrothreonine (Dht),
Vol stands for valinol,
D and E subscripts stand for D-form chirality in an amino acid and (E)-configuration respectively,
and % indicates relative abundance of a variant among the BT NRP variants as a mixture isolated from *B. texasporus* cells when assayed with mass spectrometry)

EXAMPLE 1

Mass Spectrometry

In WO/2005/074626 and (Wu et al., 2005), the NRPS codon of the first module of the BT's non-ribosomal peptide synthetase was predicted to be that of threonine or dehydrothreonine (Dht). Since the standard amino acid composition assays of BT1583 failed to produce evidence for the presence of either Thr or Dht as the first amino acid residue, a residue of Bmt was tentatively assigned merely because its doubly N-methylated form could provide a fragment with a mass of 197 which roughly "fit" the b-series m/z signal of 198 in tandem mass spectrometry (MS/MS).

To gain better insight into the N-terminal structure, BT1583 peptide was subjected to a more comprehensive MS/MS analysis, which revealed a previously undetected smaller b-series m/z signal of 115.1 that would translate into a ΔM of 83.0 daltons as the mass for the first amino acid residue (Table 2). The only known amino acid residue with a mass of 83.0 daltons is exactly dehydrothrenine (Dht), which is more commonly known in literatures as 2,3-dehydro-2-aminobutyric acid (Dhb).

TABLE 2

MS/MS results of C18 HPLC purified BT NRP variants

| BT1583 | | | BT1569-V2 | | | BT1597-I5 | | |
|---|---|---|---|---|---|---|---|---|
| Mass m/z b-series | ΔM | Predicted residue | Mass m/z b-series | ΔM | Predicted residue | Mass m/z b-series | ΔM | Predicted residue |
| 115.1 | 115.1 | Hmp | 115.1 | 115.1 | Hmp | 115.1 | 115.1 | Hmp |
| 198.1 | 83.0 | Dhb | 198.1 | 83.0 | Dhb | 198.1 | 83.0 | Dhb |
| 311.2 | 113.1 | Leu | 297.1 | 99.0 | ***Val*** | 311.2 | 113.1 | Leu |
| 425.2 | 114.0 | Orn | 411.2 | 114.1 | Orn | 425.2 | 114.0 | Orn |
| 538.3 | 113.1 | Ile | 524.3 | 113.2 | Ile | 538.3 | 113.1 | Ile |
| 637.3 | 99.0 | Val | 623.3 | 99.0 | Val | 651.3 | 113.0 | ***Ile*** |
| 736.3 | 99.1 | Val | 722.3 | 99.0 | Val | 750.4 | 99.1 | Val |
| 864.4 | 128.0 | Lys | 850.4 | 128.1 | Lys | 878.4 | 128.0 | Lys |
| 963.5 | 99.1 | Val | 949.4 | 99.0 | Val | 977.5 | 99.1 | Val |
| 1076.5 | 113.0 | Leu | 1062.5 | 113.1 | Leu | 1090.5 | 113.0 | Leu |
| 1204.6 | 128.1 | Lys | 1190.5 | 128.0 | Lys | 1218.6 | 128.1 | Lys |
| 1367.7 | 163.1 | Tyr | 1353.6 | 163.1 | Tyr | 1381.7 | 163.1 | Tyr |
| 1480.8 | 113.1 | Leu | 1466.8 | 113.2 | Leu | 1494.8 | 113.1 | Leu |
| 1583.0 | 102.2 | Vol | 1569.0 | 102.2 | Vol | 1597.0 | 102.2 | Vol |

| BT1555-V2V4 | | | BT1601-M2 | | | BT1611-K3I5 | | |
|---|---|---|---|---|---|---|---|---|
| Mass m/z b-series | ΔM | Predicted residue | Mass m/z b-series | ΔM | Predicted residue | Mass m/z b-series | ΔM | Predicted residue |
| 115.1 | 115.1 | Hmp | 115.1 | 115.1 | Hmp | 115.1 | 115.1 | Hmp |
| 198.1 | 83.0 | Dhb | 198.1 | 83.0 | Dhb | 198.1 | 83.0 | Dhb |
| 297.1 | 99.0 | ***Val*** | 329.1 | 131.0 | ***Met*** | 311.2 | 113.1 | Leu |
| 411.2 | 114.1 | Orn | 443.2 | 114.1 | Orn | 439.3 | 128.1 | ***Lys*** |
| 510.2 | 99.0 | ***Val*** | 556.2 | 113.0 | Ile | 552.3 | 113.0 | Ile |
| 609.3 | 99.1 | Val | 655.3 | 99.1 | Val | 665.3 | 113.0 | ***Ile*** |
| 708.3 | 99.0 | Val | 754.3 | 99.0 | Val | 764.4 | 99.1 | Val |
| 836.4 | 128.1 | Lys | 882.4 | 128.1 | Lys | 892.4 | 128.0 | Lys |
| 935.4 | 99.0 | Val | 981.4 | 99.0 | Val | 991.5 | 99.1 | Val |
| 1048.5 | 113.1 | Leu | 1094.5 | 113.1 | Leu | 1104.5 | 113.0 | Leu |
| 1176.5 | 128.0 | Lys | 1222.5 | 128.0 | Lys | 1232.6 | 128.1 | Lys |
| 1339.6 | 163.1 | Tyr | 1385.6 | 163.1 | Tyr | 1395.7 | 163.1 | Tyr |
| 1452.7 | 113.1 | Leu | 1498.8 | 113.2 | Leu | 1508.8 | 113.1 | Leu |
| 1555.0 | 102.3 | Vol | 1601.0 | 102.2 | Vol | 1611.0 | 102.2 | Vol |

| BT1615-M2I5 | | | BT1583-I2 | | | BT1617-F2 | | |
|---|---|---|---|---|---|---|---|---|
| Mass m/z b-series | ΔM | Predicted residue | Mass m/z b-series | ΔM | Predicted residue | Mass m/z b-series | ΔM | Predicted residue |
| 115.1 | 115.1 | Hmp | 115.1 | 115.1 | Hmp | 115.1 | 115.1 | Hmp |
| 198.1 | 83.0 | Dhb | 198.1 | 83.0 | Dhb | 198.1 | 83.0 | Dhb |
| 329.1 | 131.0 | ***Met*** | 311.1 | 113.0 | ***Ile*** | 345.1 | 147.0 | ***Phe*** |
| 443.2 | 114.1 | Orn | 425.2 | 114.1 | Orn | 459.2 | 114.1 | Orn |
| 556.2 | 113.0 | Ile | 538.2 | 113.0 | Ile | 572.2 | 113.0 | Ile |
| 669.3 | 113.1 | ***Ile*** | 637.3 | 99.1 | Val | 671.3 | 99.1 | Val |
| 768.3 | 99.0 | Val | 736.3 | 99.0 | Val | 770.3 | 99.0 | Val |
| 896.4 | 128.1 | Lys | 864.3 | 128.0 | Lys | 898.4 | 128.1 | Lys |
| 995.4 | 99.0 | Val | 963.4 | 99.1 | Val | 997.4 | 99.0 | Val |
| 1108.5 | 113.1 | Leu | 1076.4 | 113.0 | Leu | 1110.4 | 113.0 | Leu |
| 1236.5 | 128.0 | Lys | 1204.5 | 128.1 | Lys | 1238.5 | 128.1 | Lys |
| 1399.6 | 163.1 | Tyr | 1367.6 | 163.1 | Tyr | 1401.5 | 163.0 | Tyr |
| 1512.8 | 113.2 | Leu | 1480.7 | 113.1 | Leu | 1514.6 | 113.1 | Leu |
| 1615.0 | 102.2 | Vol | 1583.0 | 102.3 | Vol | 1617.0 | 102.4 | Vol |

The identification of BT1583's first amino acid residue as Dhb raised the possibility that BT1583 and the lipopeptide bogorol A have the same molecular structure. As an initial test of this hypothesis, BT1583 was hydrolysed to free amino acids with HC1 at 110° C. overnight and then subjected to MALDI-TOF mass spectrometry to see whether BT1583 also contained Dhb and Hmp residues. In the positive mode of detection, although Tyr ($M+H^+/z$ =182.1), Lys (147.1), Orn (133.1), Leu/Ile (132.1), Val (118.1) and Vol (104.1) were clearly detected, Dhb/Dht (102.1) or Thr (120.1) remained undetected. However, in the negative mode of detection, an $M-H^+/z$ signal of 131.1 was clearly detected to corroborate the presence of an Hmp residue in BT1583.

HPLC purification allowed isolation of eight additional BT NRP variants, and they were also subjected to the same comprehensive MS/MS analysis. Since all these NRP variants produced a b-series m/z signal of 115.1 besides 198.1 (Table 2), they appeared to contain the same N-terminal (Hmp-Dhb-) structure as BT1583.

Therefore, the mass spectrometry results revealed additional structural similarity of BT peptides to the bogorol lipopeptides and called for further investigation to determine the exact relationship between the two families of peptides.

EXAMPLE 2

2D NMR

Two-dimensional NMR spectroscopy on an acetylated derivative of bogorol A played a key role in solving the structure of bogorol A (U.S. Pat. No. 6,784,283). To comprehensively elucidate the structure of native BT1583, two-dimensional NMR spectroscopy was successfully performed on non-derivatized BT1583. The NMR data revealed 14 spin systems corresponding to 13 amino acid residues (one of Dhb, three of Leu, one of Orn, one of Ile, three of Val, two of Lys, one of Tyr, and one of Vol) plus one fatty acid residue of Hmp. Complete resonance assignments was made (Table 3) based on the reported chemical shift values for amino acids, Hmp and Vol as well as from $^1H$-$^1H$ total correlation spectroscopy (TOCSY), $^1H$-$^1H$ correlated spectroscopy (COSY), $^1H$-$^{15}N$ heteronuclear single quantum coherence (HSQC) and $^1H$-$^{13}C$ heteronuclear multiple-quantum coherence (HMQC) experiments, which allowed identification of all 14 spin systems. Nuclear overhauser enhancement spectroscopy (NOESY) map spectra showed cross-peaks due to dipolar connectivities. NHi/NH(i+1) and/or Cαkli/NH(i+1) cross-peaks, where i designates a numerical position of an amino acid, allowed determination of the amino acid sequence and the N-terminal attachment of Hmp0 to Dhb1 (FIG. 1).

TABLE 3

$^1H$ and $^{13}C$ NMR data for BT1583 at 500 MHz

| Residue | Assignment | $^{13}C$ δ (ppm) | $^1H$ δ (ppm) | NOESY | COSY | TOCSY |
|---|---|---|---|---|---|---|
| Hmp0 | C2 | 74.2 | 3.59 | Dhb1-NH, C6 | C3, OH | C3, C4, C5, C6, OH |
| | C3 | 37.9 | 1.48 | | C2, C4, C6 | C2, C4, C5, C6 |
| | C4 | 26.1 | 1.16, 0.90 | | C3, C5 | C2, C3, C5, C6 |
| | C5 | 14.9 | 0.58 | | C4 | C2, C3, C4, C5 |
| | C6 | 15.0 | 0.65 | C2 | C3 | C2, C3, C4, C6 |
| | OH | — | 5.38 | | C2 | C2 |
| Dhb1 | NH | — | 9.05 | Hmp0-C2, Leu2-NH | Cβ, Cγ | Cγ |
| | Cα | n.d. | — | | | |
| | Cβ | 117.8 | 5.58 | | NH, Cγ | Cγ |
| | Cγ | 12.4 | 1.51 | Leu2-NH, Leu2-Cα | NH, Cβ | NH, Cβ |
| Leu2 | NH | — | 7.99 | Dhb1-NH, Dhb1-Cγ, Orn3-NH | Cα | Cα, Cβ, Cγ, Cδ |
| | Cα | 51.8 | 4.08 | Dhb1-Cγ, Orn3-NH | NH, Cβ, Cγ | NH, Cβ, Cγ, Cδ |
| | Cβ | 37.8 | 1.44 | | Cα, Cγ, Cδ | NH, Cα, Cγ, Cδ |
| | Cγ | 23.9 | 1.33 | | Cα, Cβ, Cδ | NH, Cα, Cβ, Cδ |
| | Cδ | 22.9 | 0.65, 0.62 | | Cβ, Cγ | NH, Cα, Cβ, Cγ |
| Orn3 | NH | — | 7.81 | Leu2-NH, Leu2-Cα, Ile4-NH | Cα | Cα, Cβ, Cγ, Cδ |
| | Cα | 51.2 | 4.14 | Ile4-NH | NH, Cβ, Cγ | NH, Cβ, Cγ, Cδ |
| | Cβ | 28.8 | 1.47, 1.43 | | Cα, Cγ | NH, Cα, Cγ, Cδ, $NH_2$ |
| | Cγ | 23.8 | 1.34 | | Cα, Cβ, Cδ | NH, Cα, Cβ, Cδ, $NH_2$ |
| | Cδ | 38.1 | 2.53 | | Cγ, $NH_2$ | NH, Cα, Cβ, Cγ, $NH_2$ |
| | $NH_2$ | — | 7.50 | | Cδ | Cβ, Cγ, Cδ |
| Ile4 | NH | — | 7.57 | Orn3-NH, Orn3-Cα, Val5-NH | Cα | Cα, Cβ, Cδ1, Cγ2 |
| | Cα | 55.9 | 4.08 | Val5-NH | NH, Cβ, Cγ1 | NH, Cβ, Cγ2 |
| | Cβ | 36.3 | 1.50 | | Cα, Cγ1, Cδ1, Cγ2 | NH, Cα, Cγ1, Cδ1, Cγ2 |
| | Cγ1 | 21.7 | 1.15, 0.81 | | Cα, Cβ, Cδ1, | Cβ, Cδ1, Cγ2 |
| | Cδ1 | 10.5 | 0.53 | | Cβ, Cγ1 | NH, Cβ, Cγ1 |
| | Cγ2 | 11.2 | 0.57 | | Cβ, Cδ1 | Cα, Cβ, Cγ1 |
| Val5 | NH | — | 7.76 | Ile4-NH, Ile4-Cα, Val6-NH | Cα | Cα, Cβ, Cγ |
| | Cα | 57.3 | 3.93 | Val6-NH | NH, Cβ | NH, Cβ, Cγ |
| | Cβ | 29.8 | 1.72 | | Cα, Cγ | NH, Cα, Cγ |
| | Cγ | 19.4, 19.0 | 0.60 | | Cβ | NH, Cα, Cβ |
| Val6 | NH | — | 7.57 | Val5-NH, Val5-Cα, Lys7-NH | Cα | Cα, Cβ, Cγ |
| | Cα | 57.4 | 3.98 | Lys7-NH | NH, Cβ | NH, Cβ, Cγ |
| | Cβ | 30.2 | 1.74 | | Cα, Cγ | NH, Cα, Cγ |
| | Cγ | 18.2, 17.9 | 0.59 | | Cβ | NH, Cα, Cβ |

TABLE 3-continued

| $^1$H and $^{13}$C NMR data for BT1583 at 500 MHz | | | | | | |
|---|---|---|---|---|---|---|
| Residue | Assignment | $^{13}$C δ (ppm) | $^1$H δ (ppm) | NOESY | COSY | TOCSY |
| Lys7 | NH | — | 7.79 | Val6-NH, Val6-Cα, Val8-NH | Cα | Cα, Cβ, Cγ, Cδ |
| | Cα | 51.9 | 4.08 | Val8-NH | NH, Cβ | NH, Cβ, Cγ, Cδ |
| | Cβ | 28.5 | 1.43 | | Cα, Cγ | NH, Cα, Cγ, Cδ, Cε, $NH_2$ |
| | Cγ | 22.0 | 1.04 | | Cβ, Cδ | NH, Cα, Cβ, Cδ, Cε, $NH_2$ |
| | Cδ | 26.2 | 1.27 | | Cγ, Cε | NH, Cα, Cβ, Cγ, Cε, $NH_2$ |
| | Cε | 38.2 | 2.48 | | Cδ, $NH_2$ | Cβ, Cγ, Cδ, Cε, $NH_2$ |
| | $NH_2$ | — | 7.51 | | Cε | Cβ, Cγ, Cδ, Cε |
| Val8 | NH | — | 7.59 | Lys7-NH, Lys7-Cα, Leu9-NH | Cα | Cα, Cβ, Cγ |
| | Cα | 57.1 | 4.01 | Leu9-NH | NH, Cβ | NH, Cβ, Cγ |
| | Cβ | 30.2 | 1.78 | | Cα, Cγ | NH, Cα, Cγ |
| | Cγ | 17.4, 17.3 | 0.56 | | Cβ | NH, Cα, Cβ |
| Leu9 | NH | — | 7.87 | Val8-NH, Val8-Cα, Lys10-NH | Cα | Cα, Cβ, Cγ, Cδ |
| | Cα | 50.8 | 4.07 | Lys10-NH | NH, Cβ, Cγ | NH, Cβ, Cγ, Cδ |
| | Cβ | 39.8 | 1.32 | | Cα, Cγ, Cδ | NH, Cα, Cγ, Cδ |
| | Cγ | 23.8 | 1.24 | | Cα, Cβ, Cδ | NH, Cα, Cβ, Cδ |
| | Cδ | 22.9 | 0.63, 0.58 | | Cβ, Cγ | NH, Cα, Cβ, Cγ |
| Lys10 | NH | — | 7.80 | Leu9-NH, Leu9-Cα, Tyr11-NH | Cα | Cα, Cβ, Cγ, Cδ |
| | Cα | 51.4 | 4.00 | Tyr11-NH | NH, Cβ | NH, Cβ, Cγ, Cδ |
| | Cβ | 31.2 | 1.21 | | Cα, Cγ | NH, Cα, Cγ, Cδ, Cε, $NH_2$ |
| | Cγ | 21.8 | 0.82 | | Cβ, Cδ | NH, Cα, Cβ, Cδ, Cε, $NH_2$ |
| | Cδ | 23.1 | 1.12 | | Cγ, Cε | NH, Cα, Cβ, Cγ, Cε, $NH_2$ |
| | Cε | 38.2 | 2.44 | | Cδ, $NH_2$ | Cβ, Cγ, Cδ, Cε, $NH_2$ |
| | $NH_2$ | — | 7.54 | | Cε | Cβ, Cγ, Cδ, Cε |
| Tyr11 | NH | — | 7.95 | Lys10-NH, Lys10-Cα, Leu12-NH | Cα | Cα, Cβ |
| | Cα | 54.2 | 4.23 | Leu12-NH | NH, Cβ | NH, Cβ |
| | Cβ | 38.2 | 2.62, 2.45 | | Cα | NH, Cα |
| | Cγ | n.d. | — | | | |
| | Cδ | 130.3 | 6.77 | | Cε, OH | Cε, OH |
| | Cε | 115.0 | 6.38 | | Cγ, OH | Cγ, OH |
| | Cζ | n.d. | — | | | |
| | OH | — | 9.35 | | Cδ, Cε | Cδ, Cε |
| Leu12 | NH | — | 7.91 | Tyr11-NH, Tyr11-Cα, Vol13-NH | Cα | Cα, Cβ, Cγ, Cδ |
| | Cα | 50.7 | 3.98 | Vol13-NH | NH, Cβ, Cγ | NH, Cβ, Cγ, Cδ |
| | Cβ | 40.6 | 1.15 | | Cα, Cγ, Cδ | NH, Cα, Cγ, Cδ |
| | Cγ | 23.5 | 1.04 | | Cα, Cβ, Cδ | NH, Cα, Cβ, Cδ |
| | Cδ | 21.2 | 0.57, 0.52 | | Cβ, Cγ | NH, Cα, Cβ, Cγ |
| Vol13 | NH | — | 7.21 | Leu12-NH, Leu12-Cα | Cα | Cα, Cβ1, Cγ1, Cγ1', Cβ2 |
| | Cα | 55.2 | 3.31 | | NH, Cβ1, Cβ2 | NH, Cβ1, Cγ1, Cγ1', Cβ2 |
| | Cβ1 | 27.9 | 1.59 | | Cα, Cγ1, Cγ1' | NH, Cα, Cγ1, Cγ1', Cβ2 |
| | Cγ1 | 21.2 | 0.62 | | Cβ1 | NH, Cα, Cβ1, Cβ2 |
| | Cγ1' | 20.7 | 0.57 | | Cβ1 | NH, Cα, Cβ1, Cβ2 |
| | Cβ2 | 60.8 | 3.13 | | Cα | NH, Cα, Cγ1, Cγ1', Cβ1 |
| | OH | — | n.d. | | | |

In particular, in the olefinic spectral region, the signature quartet of intensity 1:3:3:1 (around $^1$H δ=5.58 ppm) was straightforwardly assigned to the Dhb1 Cβ proton. The Dhb1's (E)-configuration assignment was made on the basis of the Dhb1Cγ protons' NOE coupling to the Leu2 NH proton.

Key features of Hmp0 were confirmed by the TOCSY, COSY and HMQC experiments. A proton ($^1$H δ=5.38 ppm) was identified as a hydroxyl proton based on its being attached to neither carbon (in $^1$H-$^{13}$C HMQC) nor nitrogen (for its relative low δ). In both $^1$H-$^1$H COSY and $^1$H-$^1$H TOCSY, the hydroxyl proton was found to be interacting only with the Hmp C2 proton ($^1$H δ=3.59 ppm). The branched nature of Hmp at C3 was demonstrated by the C6 methyl protons' exclusive COSY interaction with the C3 proton which in turn showed additional COSY interactions with the C2 and C4 protons. Finally, the NOE coupling between the C2 and C6 protons was fully consistent with an L-Hmp residue.

Therefore, BT1583 and bogorol A have the same structure of Hmp-$_E$Dhb-Leu-$_D$Orn-Ile-Val-Val-$_D$Lys-Val-$_D$Leu-Lys-$_D$Tyr-Leu-Vol (SEQ ID NO:1). In other words, BT1583 and its natural NRP variants from *B. texasporus* are not N-terminally methylated as described and claimed in WO/2005/074626. This conclusion has been incorporated into the description of natural BT NRP variants in Table 1 (with correlations to bogorol peptides except bogorol E which is apparently an oxidized derivative of bogorol D).

Accordingly, despite its vastly different native habitat, *Brevibacillus laterosporus* PNG276 is also a strain of the *B. texasporus* subspecies based on its production of the BT family of peptides.

EXAMPLE 3

BT and TLR2

Orally delivered BT lipopeptides prime (rather than directly active) chicken blood innate immunity cells of heterophils and monocytes (Kogut et al., 2007; Kogut et al., 2009), and BT lipopeptides also prime (rather than directly active) isolated chicken heterophils and monocytes in vitro (Kogut et al., 2012). Since orally delivered BT lipopeptides are not absorbed into blood to come into direct contact with these innate immunity cells, BT's in vitro priming of leukocytes by no means suggests that BT lipopeptides do the same in vivo. However, the in vitro priming assay provides a useful tool for probing possible signaling pathway involved in BT-mediated innate immunomodulation. Since TLRs are conserved receptors playing key roles in innate immunity (Farnell et al., 2003) and TLR2 is the only TLR that has lipopeptide agonists, the same in vitro BT priming assay (Kogut et al., 2012) was employed to investigate whether TLR2 can function as a receptor for BT lipopeptides.

Goat polyclonal antibodies raised against human TLR2 were purchased from Santa Cruz Biotechnology Lab (Santa Cruz, Calif.). For TLR2-blocking, isolated chicken heterophils and the antibodies (2.0 μg/ml) were incubated, prior to the treatments of BT and/or PMA, at 39° C. for 30 minutes.

TABLE 4

PMA-stimulated oxidative burst of heterophils in vitro

| Group | Step I. Anti-TLR2 antibody blocking (30 min) | Step II. 12 ppm BT treatment (60 min) | Step III. PMA stimulation | Step IV. Oxidative burst (RFU + SE) in $10^3$ |
|---|---|---|---|---|
| 1 | − | − | − | 3.244 ± 0.157 |
| 2 | − | − | + | 11.235 ± 0.125 |
| 3 | − | + | − | 3.549 ± 0.05 |
| 4 | − | + | + | 31.927 ± 0.168 |
| 5 | + | − | + | 11.6 ± 0.07 |
| 6 | + | + | + | 18.165 ± 0.095 |

As previously reported, treatment of heterophils with BT lipopeptides (12 ppm) did not stimulate oxidative burst in the absence of PMA (Group 3 versus Group 1, Table 4), but significantly increased PMA-stimulated oxidative burst by about 3-fold (Group 4 versus Group 2).

Pre-treatment of heterophils with the goat anti-human TLR2 antibodies (2.0 μg/ml) decreased BT-primed oxidative burst (Group 6 versus Group 4) by 43%, which is at the maximal reported level of inhibition by these human antibodies on chicken TLR2 (Farnell et al., 2003). These results demonstrated that antibodies against human TLR2 at least partially block BT's priming of heterophils to support the idea of TLR2 functioning as a receptor for in vitro priming of purified by BT lipopeptides and BT lipopeptides being (priming-only) noninflammatory TLR2 agonists.

EXAMPLE 4

BT Lipopeptides as an Oral Adjuvant

Since traditional inflammatory TLR2 agonists have been used as adjuvants for various vaccines, the discovery of BT lipopeptides as noninflammatory TLR2 agonists prompted a classic adjuvant efficacy test for their in vivo immunomodulatory activities in a mouse TB vaccination model. C57BL/6 mice were first treated with oral BT lipopeptides and then one of two TB vaccines (the relatively weak ESAT-6/MPL/DDA subunit vaccine and the robust live BCG vaccine) and then tested for an improved response to the vaccine treatment. The test groups included:

1. Oral BT lipopeptide treatment, administered at 40 ppm in the drinking water for 3 days alone;
2. Oral BT lipopeptide treatment (40 ppm in drinking water) for 3 days, followed by ESAT-6/MPL/DDA injection on the 3rd day at a 1× concentration;
3. ESAT-6/MPL/DDA injection at a 1× alone;
4. Oral BT lipopeptide treatment (40 ppm in drinking water) for 3 days, followed by MPL/DDA injection on the 3rd day at a 1× concentration;
5. Oral BT lipopeptide treatment (40 ppm in drinking water) for 3 days, followed by injection of a BCG vaccine on the 3rd day;
6. BCG vaccine injection alone;
7. MPL/DDA injection alone; and
8. Saline injection alone.

Mice were inoculated as above and rested for 4 weeks and then challenged with a low dose aerosol (50-100 CFU) of virulent *M. tuberculosis* H37Rv. The number of viable bacilli 30 days post challenge was then assessed. At day 30 post-infection a viable count was performed on the lung and spleen of mice by homogenizing the organs and plating serial 10-fold dilutions on 7H11 agar plates.

TABLE 5

Testing of the adjuvant activities of BT lipopeptides for TB vaccines

| Group | Lung | | | Spleen | | |
|---|---|---|---|---|---|---|
| | Mean $Log_{10}$ CFU | std | $Log_{10}$ CFU Reduction | Mean $Log_{10}$ CFU | std | $Log_{10}$ CFU Reduction |
| 1. BT | 6.13 | 0.30 | 0.00 | 5.15 | 0.75 | −0.34 |
| 2. BT + ESAT-6/MPL/DDA | 5.06 | 0.61 | 1.07 | 4.24 | 0.75 | 0.57 |

TABLE 5-continued

Testing of the adjuvant activities of BT lipopeptides for TB vaccines

| | Lung | | | Spleen | | |
|---|---|---|---|---|---|---|
| Group | Mean $Log_{10}$ CFU | std | $Log_{10}$ CFU Reduction | Mean $Log_{10}$ CFU | std | $Log_{10}$ CFU Reduction |
| 3. ESAT-6 + MPL/DDA | 5.76 | 0.35 | 0.38 | 4.71 | 0.64 | 0.10 |
| 4. BT + MPL/DDA | 6.28 | 0.19 | −0.14 | 5.34 | 0.51 | −0.53 |
| 5. BT + BCG | 5.08 | 0.45 | 1.06 | 3.31 | 0.46 | 1.50 |
| 6. BCG | 5.24 | 0.14 | 0.90 | 3.36 | 0.80 | 1.45 |
| 7. MPL/DDA | 6.15 | 0.37 | −0.01 | 4.87 | 0.87 | −0.06 |
| 8. Saline | 6.14 | 0.16 | N/A | 4.81 | 0.45 | N/A |

N/A = Not Applicable.
Log10 CFU reduction = Mean Log10 CFU for the saline group − Mean Log10 CFU for the treatment group.

The results shown in Table 5 demonstrated that BT lipopeptides orally delivered at 40 ppm in drinking water for three days significantly increased the effectiveness of the ESAT-6 subunit vaccine (especially in lung the target organ of) to the level of the live BCG vaccine (even when the BT adjuvant was delivered separately from the vaccine), confirming oral BT lipopeptides' robust anti-infective immunomodulatory activity in C57BL/6 mice at this dosing level of 40 ppm in drinking water.

EXAMPLE 5

BT-mediated Immunomodulation is not Sufficient to Confer Anti-diabesity Activities The above finding of BT lipopeptides being TLR2 agonists seemed to reinforce the idea that BT peptides being obesogenic, because TLR2 signaling mediates diet-induced obesity (DIO) and metabolic syndrome in a mouse model (Ehses et al., 2010; Himes and Smith, 2010; Kuo et al., 2011). A DIO mouse study was performed to examine the effects of orally delivered BT lipopeptides at a highly immunomodulatory level (40 ppm in drinking water, as established by the classic adjuvant test in Example 4) on obesity and metabolic syndrome.

High-fat diet-induced obese C57BL/6 mice were used for evaluation of BT peptides' effects. Animals were 18 week-old and had been on ad libitum high-fat diet for 12 weeks prior to treatment. The animals' level of obesity was intermediary (weighing about 40 grams) to allow assessment of the lipopetides' effect on body weight/obesity in both directions. The animals were fed with the high-fat diet D12492 (60% kcal % fat) from Research Diets Inc. Baseline measurements (weekly food and water intake, body weight, blood glucose, insulin, oral glucose tolerance test) were performed prior to treatment with natural BT peptides. Two randomized groups were formed [Control (non-peptide treated) and Experimental (BT peptides treated)]. BT peptides were delivered in drinking water at 40 ppm or 40 mg/L. Effects of BT lipopeptides (on food and water intake, body weight, blood glucose, insulin and oral glucose tolerance) were evaluated.

Figure 2:
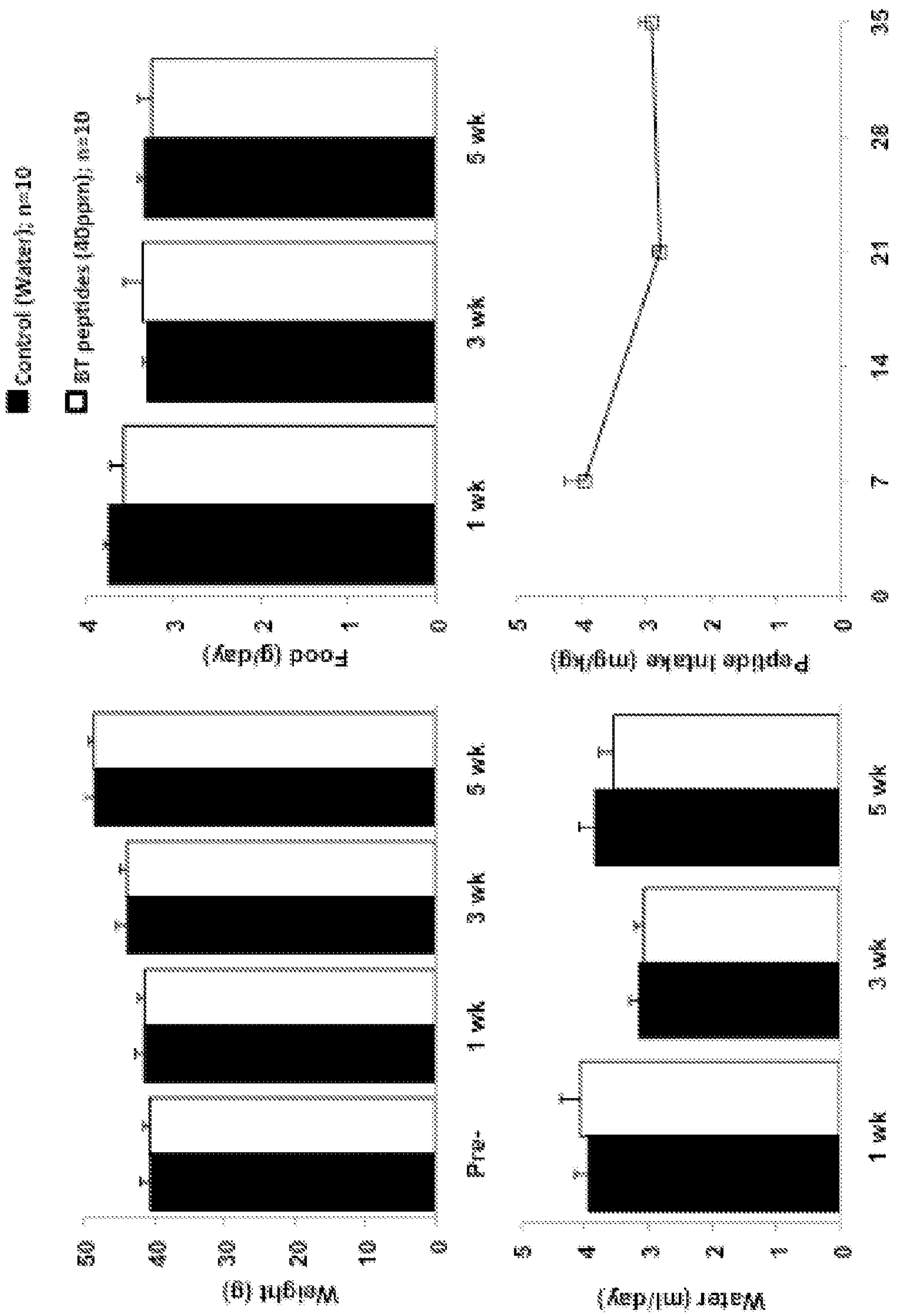

As shown in FIG. 2, oral BT treatment via drinking water at 40 ppm for 5 weeks caused no difference in weight gain, food intake or water intake of the DIO mice. The equivalent BT in-food delivery concentration remained constant at about 40 ppm (or mg per kg of food) throughout the study.

Figure 3:
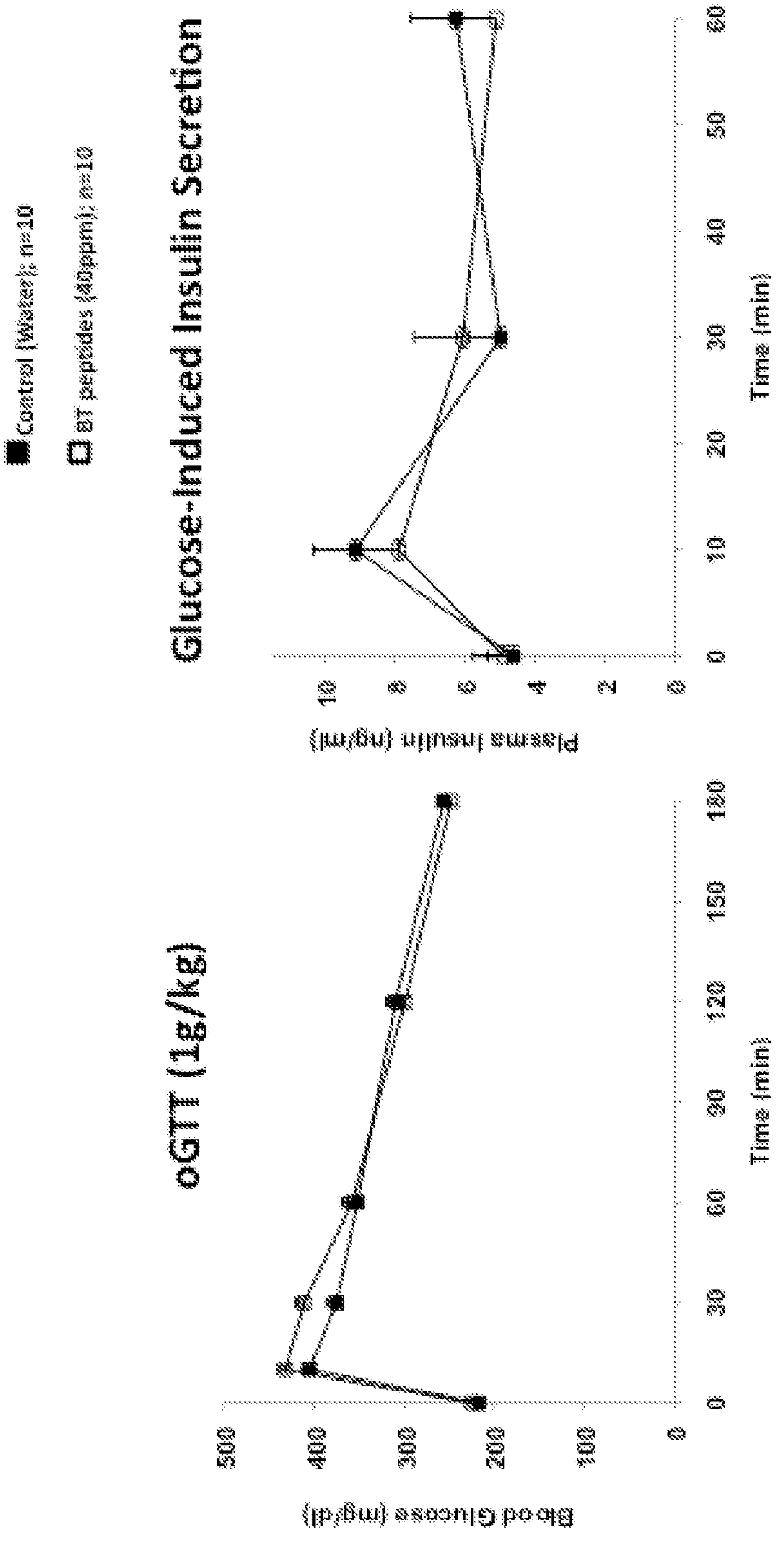

As shown in FIG. 3, the oral BT treatment via drinking water at 40 ppm for 5 weeks caused no difference in blood glucose level control or insulin sensitivity of the DIO mice. Orally delivery BT lipopeptides at a level sufficient for effective in vivo modulation of anti-infective innate immunity failed to change diet-induced obesity or insulin resistance in either direction, to corroborate intestinal immune tolerance (an absent role of TLR-mediated anti-infective innate immunity in controlling symbiotic commensal-mediated diabesity).

EXAMPLE 6

Anti-diabesity Effects of Orally Delivered BT Lipopeptides as a Pseudo-nutrient in DIO Mice The discovery of BT lipopeptides as noninflammatory TLR2 agonists made an unexpected and diametrically-opposed prediction of their utilities as anti-diabesity pseudo-nutrients via the TLR-mediated nutrient-sensing in enteroendocrine/taste receptor cells ("the BT-enteroendocrine hypothesis"). Since the threshold to induce a GI hormonal response appears to be high, as minimally 8% (or 80,000 ppm, 3 orders of magnitude higher than any BT concentration tested then) resistant starch in diet is needed to increase plasma GLP-1 and PYY (Belobrajdic et al., 2012), the BT concentration (in drinking water) was elevated by one order of magnitude from 40 ppm to 400 ppm in a new test for possible anti-diabesity effects in DIO mice.

The C57BLK/6 DIO mice were 24 week-old and had been on D12492 ad libitum for 18 weeks prior to treatment, and they were extremely obese and weighed at about 50 grams at the beginning of the study. Baseline measurements (weekly food and water intake, body weight, blood glucose, insulin, oral glucose tolerance test) were performed prior to treatment. A Control group (10 mice) and a BT group (5 mice) were formed. BT lipopeptides were delivered in drinking water at 400 ppm or 400 mg/L for 30 days. Effects of BT lipopeptides (on food and water intake, body weight, blood glucose, insulin and oral glucose tolerance) were evaluated.

Figure 4:
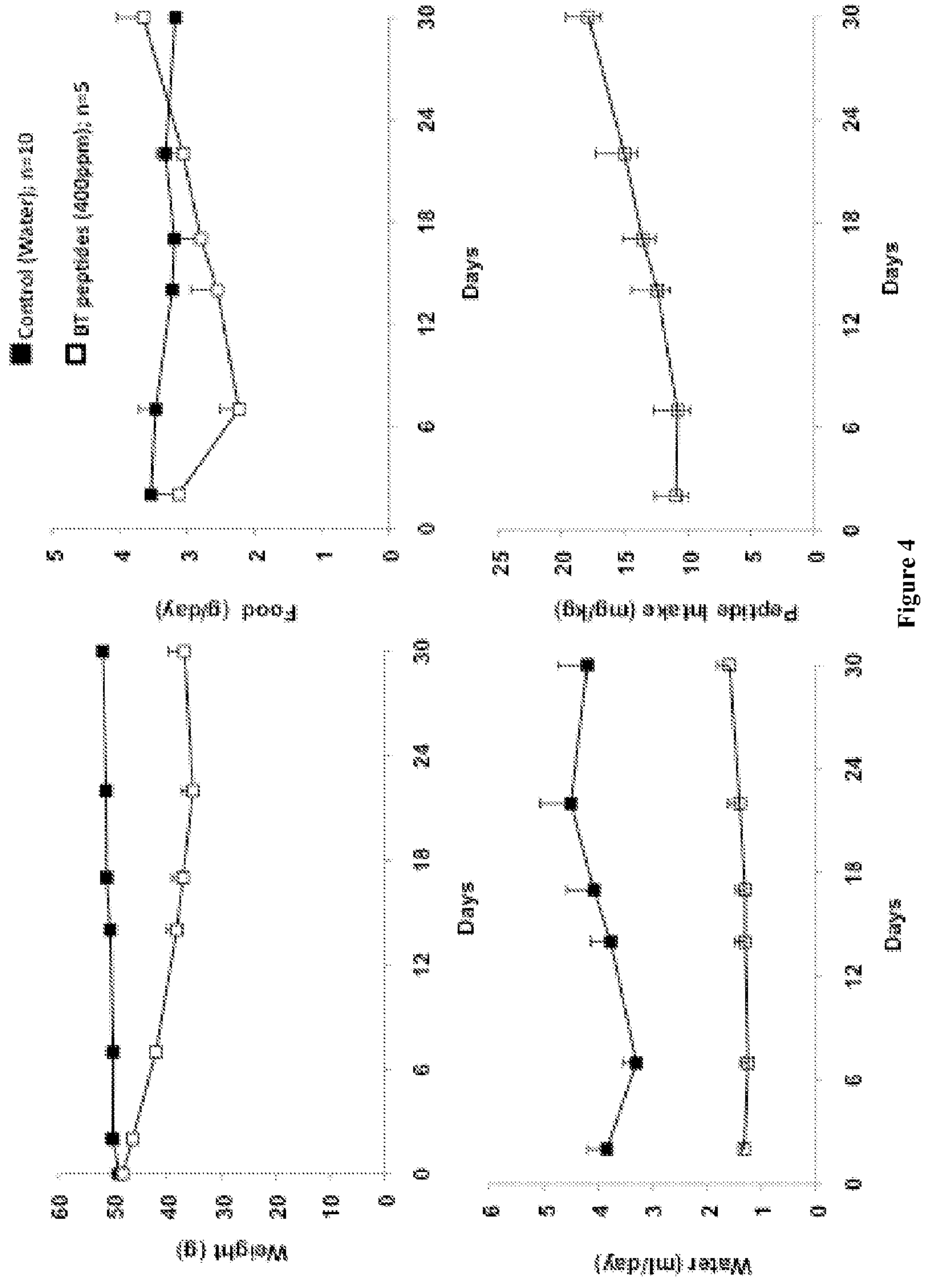

As shown in FIG. 4, oral BT treatment via drinking water at 400 ppm caused significant weight loss in DIO mice. Steady weight loss started upon BT dosing, and reached a maximum of about 15 grams or 30% of total body weight in comparison to Control around Day 22. From Day 22 to Day 30, the average body weight of the BT group remained steady at about 35 grams which is the typical body weight for healthy 27 weeks old mice fed continuously on a low-fat diet (or the normal body weight). Therefore, BT completely reversed DIO in these mice. It was also noted that BT-induced weight loss stopped exactly when the normal body weight was reached (and did not overshoot), suggesting BT's biological function being body weight normalization (optimization towards to the ideal normal weight) rather than unidirectional weight loss.

The idea of BT-mediated body weight normalization was also supported by the food intake level changes. Initially the oral BT treatment caused a steady decrease in food intake to reach a maximal 40% reduction on Day 7. After that (and over two weeks before the complete DIO reversion around Day 22), food intake started to rebound and reached the level of the Control group by Day 22. The simultaneous cessations of appetite reduction and weight loss at the normal weight underscored that appetite suppression was the key driver for weight loss and fine-tuning appetite (according to the deviation from the normal body weight) was the main mechanism for body weight normalization.

Water intake level was decreased by about two thirds throughout the study to result in equivalent BT in-food delivery concentrations about 168, 218, 200, 186, 187 and 177 ppm (or mg per kg of food) on Days 2, 7, 14, 22 and 30 respectively. In other words, the actual dosing level in this study was at about 5× of that in Example 5. Simultaneous suppression of both food and water intakes by orally delivered BT lipopetides was an outcome predicted by the BT-enteroendocrine hypothesis, because GLP-1 (Haak, 1999; Gutzwiller et al., 2004; Gutzwiller et al., 2006; McKay et al., 2011; Chan et al., 2013), PYY (Sloth et al., 2007) and CCK (Koopmans et al., 1972; Guzek and Morawska, 1986; Verbalis et al., 1987; Bondy et al., 1989; Ebenezer, 1996; Menani and Johnson, 1998) are known to suppress water intake in addition to food intake. Interestingly, invoking "conditioned taste aversion" as an alternative explanation for BT's suppression of both water and food intake would actually endorse the BT-enteroendocrine hypothesis, because conditioned taste aversion is mediated by GI hormones (Bojanowska, 2005; Chelikani et al., 2006; Schier et al., 2011) and oral taste cells (which mediate conditioned taste aversion).

Figure 5:
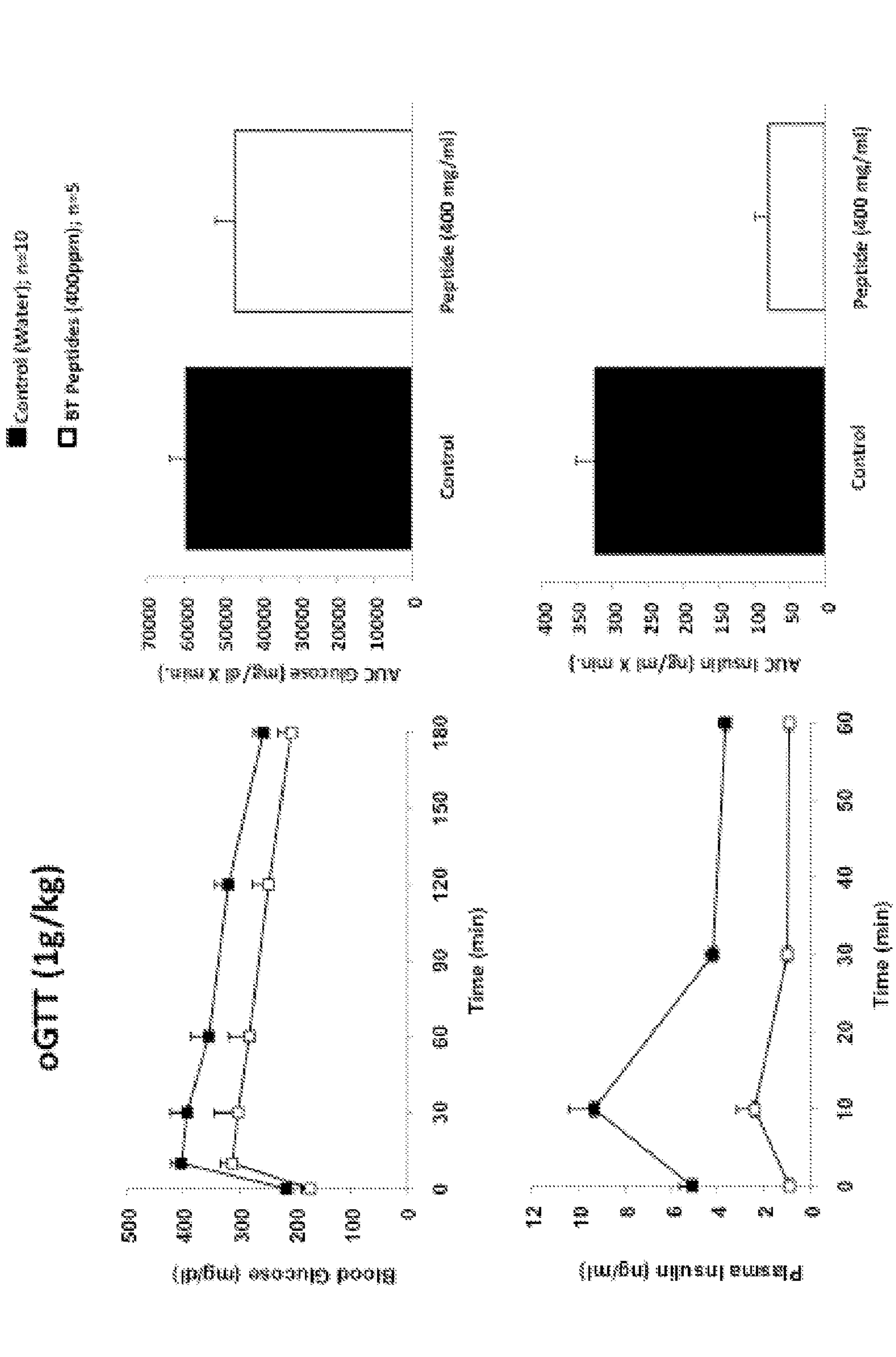

As shown in FIG. 5, the oral BT treatment via drinking water at 400 ppm for 30 days caused a significant improvement in blood glucose level control and impressive (>4-fold) enhancement of insulin sensitivity.

Figure 6:
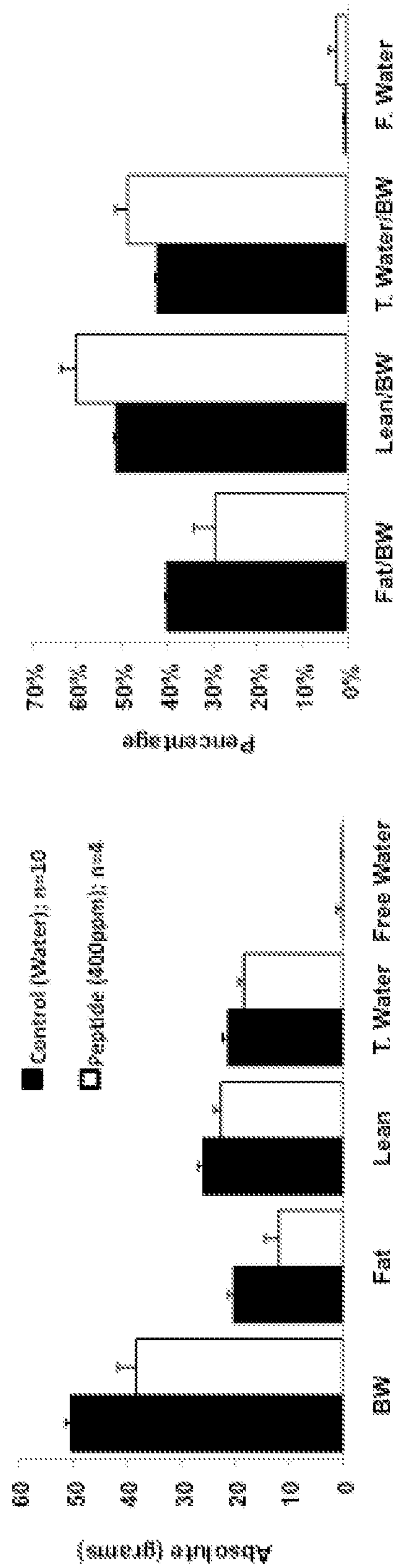

As shown in FIG. 6, the oral BT treatment caused a significant improvement in body composition with about 40% reduction in total fat mass and minimal loss of lean mass.

Importantly, the oral BT treatment maintained (both total and free) body water content, and normal body hydration with decreased water intake pointed to both increased internal water supply ("metabolic water" from fat degradation) and increased kidney water retention by CCK's induction of the antidiuretic hormone vasopressin (Guzek and Morawska, 1986; Verbalis et al., 1987). Since reduced water intake while maintaining body hydration would be a welcome benefit for diabetic patients, orally delivered BT can be used to treat diabetes-associated excessive thirst, water intake and urination. Potential adverse effects of reduced water intake in non-diabetic patients receiving oral BT can be easily avoided with physician's instruction of extra cups of water each day.

In addition, oral BT treatment for 30 days caused visible reduction in visceral obesity and improvement in fatty liver in the DIO mice. Importantly, no physiological or behavioral adverse effects were observed throughout the study.

Therefore, orally delivery of effective amount ("nutrient-sensing" level) of BT lipopeptides as a single agent caused impressive anti-diabesity effects in DIO mice in a study aiming at nutrient mimicry.

EXAMPLE 7

Anti-diabesity Effects of Orally Delivered BT Lipopeptides as a Pseudo-nutrient in db/db Mice When BT lipopetides were orally delivered to the genetically obese and diabetic db/db mice, the peptides conferred similar anti-diabesity effects. Oral delivery of BT lipopeptides via drinking water at 400 ppm (with an average daily dosing level of 15 mg per kg of body weight) dramatically reduced body weight and improved blood glucose control in db/db mice.

However, dosing db/db mice via once daily intra-gastric gavage (at 15 mg of BT lipopeptides per kg of body weight) conferred no such effects to suggest potential importance of BT lipopeptides' direct contact with or exposure to the oral cavity where GI-hormone-producing taste receptor cells reside. Due to their cationic and amphipathic characteristics, BT lipopeptides are known to be sticky to biomaterials and can be easily sequestered from the aqueous phase in vivo (U.S. 61/447,703). It is believed that when purified BT peptides are orally delivered as a water solution, the sequestration effect of the peptides by food and other gut materials can reduce the free aqueous BT lipopeptides concentration below the threshold for inducing secretion of GI hormones from the enteroendocrine cells.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein, including:

Acosta, A., Hurtado, M. D., Gorbatyuk, O., La Sala, M., Duncan, D., Aslanidi, G., Campbell-Thompson, M., Zhang, L., Herzog, H., Voutetakis, A., Baum, B. J., and Zolotukhin, S. (2011). Salivary PYY: a putative bypass to satiety. PLoS ONE 6, e26137.

Aronsson, L., Huang, Y., Parini, P., Korach-Andre, M., Hakansson, J., Gustafsson, J. A., Pettersson, S., Arulampalam, V., and Rafter, J. (2010). Decreased fat storage by *Lactobacillus paracasei* is associated with increased levels of angiopoietin-like 4 protein (ANGPTL4). PLoS ONE 5.

Backhed, F., Ding, H., Wang, T., Hooper, L. V., Koh, G. Y., Nagy, A., Semenkovich, C. F., and Gordon, J. I. (2004). The gut microbiota as an environmental factor that regulates fat storage. Proc Natl Acad Sci USA 101, 15718-15723.

Backhed, F., Manchester, J. K., Semenkovich, C. F., and Gordon, J. I. (2007). Mechanisms underlying the resistance to diet-induced obesity in germ-free mice. Proc Natl Acad Sci USA 104, 979-984.

Barsby, T., Kelly, M. T., Gagne, S. M., and Andersen, R. J. (2001). Bogorol A produced in culture by a marine *Bacillus* sp. reveals a novel template for cationic peptide antibiotics. Org Lett 3, 437-440.

Barsby, T., Warabi, K., Sorensen, D., Zimmerman, W. T., Kelly, M. T., and Andersen, R. J. (2006). The Bogorol family of antibiotics: template-based structure elucidation and a new approach to positioning enantiomeric pairs of amino acids. J Org Chem 71, 6031-6037.

Belobrajdic, D. P., King, R. A., Christophersen, C. T., and Bird, A. R. (2012). Dietary resistant starch dose-dependently reduces adiposity in obesity-prone and obesity-resistant male rats. Nutr Metab (Lond) 9, 93.

Bogunovic, M., Dave, S. H., Tilstra, J. S., Chang, D. T., Harpaz, N., Xiong, H., Mayer, L. F., and Plevy, S. E. (2007). Enteroendocrine cells express functional Toll-like receptors. Am J Physiol Gastrointest Liver Physiol 292, G1770-1783.

Bojanowska, E. (2005). Physiology and pathophysiology of glucagon-like peptide-1 (GLP-1): the role of GLP-1 in the pathogenesis of diabetes mellitus, obesity, and stress. Med Sci Monit 11, RA271-278.

Bondy, C. A., Jensen, R. T., Brady, L. S., and Gainer, H. (1989). Cholecystokinin evokes secretion of oxytocin and vasopressin from rat neural lobe independent of external calcium. Proc Natl Acad Sci USA 86, 5198-5201.

Cani, P. D., Amar, J., Iglesias, M. A., Poggi, M., Knauf, C., Bastelica, D., Neyrinck, A. M., Fava, F., Tuohy, K. M., Chabo, C., Waget, A., Delmee, E., Cousin, B., Sulpice, T., Chamontin, B., Ferrieres, J., Tanti, J. F., Gibson, G. R., Casteilla, L., Delzenne, N. M., Alessi, M. C., and Burcelin, R. (2007). Metabolic endotoxemia initiates obesity and insulin resistance. Diabetes 56, 1761-1772.

Chan, S. W., Lin, G., Yew, D. T., Yeung, C. K., and Rudd, J. A. (2013). Separation of emetic and anorexic responses of exendin-4, a GLP-1 receptor agonist in Suncus murinus (house musk shrew). Neuropharmacology 70, 141-147.

Chelikani, P. K., Haver, A. C., and Reidelberger, R. D. (2006). Dose-dependent effects of peptide YY(3-36) on conditioned taste aversion in rats. Peptides 27, 3193-3201.

Chen, J., Wang, R., Li, X. F., and Wang, R. L. (2011). *Bifidobacterium* adolescentis supplementation ameliorates visceral fat accumulation and insulin sensitivity in an experimental model of the metabolic syndrome. Br J Nutr 107, 1429-1434.

Delzenne, N. M., Neyrinck, A. M., Backhed, F., and Cani, P. D. (2011). Targeting gut microbiota in obesity: effects of prebiotics and probiotics. Nat Rev Endocrinol 7, 639-646.

Desjardine, K., Pereira, A., Wright, H., Matainaho, T., Kelly, M., and Andersen, R. J. (2007). Tauramamide, a lipopeptide antibiotic produced in culture by *Brevibacillus laterosporus* isolated from a marine habitat: structure elucidation and synthesis. J Nat Prod 70, 1850-1853.

Dyer, J., Salmon, K. S., Zibrik, L., and Shirazi-Beechey, S. P. (2005). Expression of sweet taste receptors of the T1R family in the intestinal tract and enteroendocrine cells. Biochem Soc Trans 33, 302-305.

Ebenezer, I. S. (1996). Systemic administration of cholecystokinin (CCK) inhibits operant water intake in rats: implications for the CCK-satiety hypothesis. Proc Biol Sci 263, 491-496.

Ehses, J. A., Meier, D. T., Wueest, S., Rytka, J., Boller, S., Wielinga, P. Y., Schraenen, A., Lemaire, K., Debray, S., Van Lommel, L., Pospisilik, J. A., Tschopp, O., Schultze, S. M., Malipiero, U., Esterbauer, H., Ellingsgaard, H., Rutti, S., Schuit, F. C., Lutz, T. A., Boni-Schnetzler, M., Konrad, D., and Donath, M. Y. (2010). Toll-like receptor 2-deficient mice are protected from insulin resistance and beta cell dysfunction induced by a high-fat diet. Diabetologia 53, 1795-1806.

Fak, F., and Backhed, F. (2012). *Lactobacillus reuteri* Prevents Diet-Induced Obesity, but not Atherosclerosis, in a Strain Dependent Fashion in Apoe−/− Mice. PLoS ONE 7, e46837.

Farnell, M. B., Crippen, T. L., He, H., Swaggerty, C. L., and Kogut, M. H. (2003). Oxidative burst mediated by toll like receptors (TLR) and CD14 on avian heterophils stimulated with bacterial toll agonists. Dev Comp Immunol 27, 423-429.

Field, B. C., Wren, A. M., Peters, V., Baynes, K. C., Martin, N. M., Patterson, M., Alsaraf, S., Amber, V., Wynne, K., Ghatei, M. A., and Bloom, S. R. (2010). PYY3-36 and oxyntomodulin can be additive in their effect on food intake in overweight and obese humans. Diabetes 59, 1635-1639.

Geraedts, M. C., Troost, F. J., Fischer, M. A., Edens, L., and Saris, W. H. (2010). Direct induction of CCK and GLP-1 release from murine endocrine cells by intact dietary proteins. Mol Nutr Food Res 55, 476-484.

Geraedts, M. C., Troost, F. J., and Saris, W. H. (2009). Peptide-YY is released by the intestinal cell line STC-1. J Food Sci 74, H79-82.

Gerard, J. M., Haden, P., Kelly, M. T., and Andersen, R. J. (1999). Loloatins A-D, cyclic decapeptide antibiotics produced in culture by a tropical marine bacterium. J Nat Prod 62, 80-85.

Gutzwiller, J. P., Hruz, P., Huber, A. R., Hamel, C., Zehnder, C., Drewe, J., Gutmann, H., Stanga, Z., Vogel, D., and Beglinger, C. (2006). Glucagon-like peptide-1 is involved in sodium and water homeostasis in humans. Digestion 73, 142-150.

Gutzwiller, J. P., Tschopp, S., Bock, A., Zehnder, C. E., Huber, A. R., Kreyenbuehl, M., Gutmann, H., Drewe, J., Henzen, C., Goeke, B., and Beglinger, C. (2004). Glucagon-like peptide 1 induces natriuresis in healthy subjects and in insulin-resistant obese men. J Clin Endocrinol Metab 89, 3055-3061.

Guzek, J. W., and Morawska, J. (1986). Cholecystokinin affects water intake as well as neurohypophysial storage of vasopressin and oxytocin in the rat. Exp Clin Endocrinol 88, 200-206.

Haak, T. (1999). New developments in the treatment of type 1 diabetes mellitus. Exp Clin Endocrinol Diabetes 107 Suppl 3, S 108-113.

Himes, R. W., and Smith, C. W. (2010). T1r2 is critical for diet-induced metabolic syndrome in a murine model. FASEB J 24, 731-739.

Ji, Y. S., Kim, H. N., Park, H. J., Lee, J. E., Yeo, S. Y., Yang, J. S., Park, S. Y., Yoon, H. S., Cho, G. S., Franz, C. M., Bomba, A., Shin, H. K., and Holzapfel, W. H. (2012). Modulation of the murine microbiome with a concomitant anti-obesity effect by *Lactobacillus rhamnosus* GG and *Lactobacillus sakei* NR28. Benef Microbes 3, 13-22.

Jiang, Y. W., Sims, M. D., and Conway, D. P. (2005). The efficacy of TAMUS 2032 in preventing a natural outbreak of colibacillosis in broiler chickens in floor pens. Poult Sci 84, 1857-1859.

Kadooka, Y., Sato, M., Imaizumi, K., Ogawa, A., Ikuyama, K., Akai, Y., Okano, M., Kagoshima, M., and Tsuchida, T. (2010). Regulation of abdominal adiposity by probiotics (*Lactobacillus gasseri* SBT2055) in adults with obese tendencies in a randomized controlled trial. Eur J Clin Nutr 64, 636-643.

Kang, J. H., Yun, S. I., and Park, H. O. (2010). Effects of *Lactobacillus gasseri* BNR17 on body weight and adipose tissue mass in diet-induced overweight rats. J Microbiol 48, 712-714.

Keenan, M. J., Zhou, J., McCutcheon, K. L., Raggio, A. M., Bateman, H. G., Todd, E., Jones, C. K., Tulley, R. T., Melton, S., Martin, R. J., and Hegsted, M. (2006). Effects of resistant starch, a non-digestible fermentable fiber, on reducing body fat. Obesity (Silver Spring) 14, 1523-1534.

Kogut, M. H., Genovese, K. J., He, H., Li, M. A., and Jiang, Y. W. (2007). The effects of the BT/TAMUS 2032 cationic peptides on innate immunity and susceptibility of young chickens to extraintestinal *Salmonella* enterica serovar Enteritidis infection. Int Immunopharmacol 7, 912-919.

Kogut, M. H., Genovese, K. J., He, H., Swaggerty, C. L., and Jiang, Y. W. (2012). BT cationic peptides: small peptides that modulate innate immune responses of chicken heterophils and monocytes. Vet Immunol Immunopathol 145 , 151-158.

Kogut, M. H., He, H., Genovese, K. J., and Jiang, Y. W. (2009). Feeding the BT Cationic Peptides to Chickens at Hatch Reduces Cecal Colonization by *Salmonella* enterica Serovar Enteritidis and Primes Innate Immune Cell Functional Activity. Foodborne Pathog Dis.

Kondo, S., Xiao, J. Z., Satoh, T., Odamaki, T., Takahashi, S., Sugahara, H., Yaeshima, T., Iwatsuki, K., Kamei, A., and Abe, K. (2010). Antiobesity effects of *Bifidobacterium breve* strain B-3 supplementation in a mouse model with high-fat diet-induced obesity. Biosci Biotechnol Biochem 74, 1656-1661.

Koopmans, H. S., Deutsch, J. A., and Branson, P. J. (1972). The effect of cholecystokinin pancreozymin on hunger and thirst in mice. Behav Biol 7, 441-444.

Kuo, L. H., Tsai, P. J., Jiang, M. J., Chuang, Y. L., Yu, L., Lai, K. T., and Tsai, Y. S. (2011). Toll-like receptor 2 deficiency improves insulin sensitivity and hepatic insulin signalling in the mouse. Diabetologia 54, 168-179.

Laferrere, B., Swerdlow, N., Bawa, B., Arias, S., Bose, M., Olivan, B., Teixeira, J., McGinty, J., and Rother, K. I. (2010). Rise of oxyntomodulin in response to oral glucose after gastric bypass surgery in patients with type 2 diabetes. J Clin Endocrinol Metab 95, 4072-4076.

Lammers, K. M., Brigidi, P., Vitali, B., Gionchetti, P., Rizzello, F., Caramelli, E., Matteuzzi, D., and Campieri, M. (2003). Immunomodulatory effects of probiotic bacteria DNA: IL-1 and IL-10 response in human peripheral blood mononuclear cells. FEMS Immunol Med Microbiol 38, 165-172.

Lee, H. Y., Park, J. H., Seok, S. H., Baek, M. W., Kim, D. J., Lee, K. E., Paek, K. S., and Lee, Y. (2006). Human originated bacteria, *Lactobacillus rhamnosus* PL60, produce conjugated linoleic acid and show anti-obesity effects in diet-induced obese mice. Biochim Biophys Acta 1761, 736-744.

Lee, J. Y., Sohn, K. H., Rhee, S. H., and Hwang, D. (2001). Saturated fatty acids, but not unsaturated fatty acids, induce the expression of cyclooxygenase-2 mediated through Toll-like receptor 4. J Biol Chem 276, 16683-16689.

Lee, J. Y., Zhao, L., Youn, H. S., Weatherill, A. R., Tapping, R., Feng, L., Lee, W. H., Fitzgerald, K. A., and Hwang, D. H. (2004). Saturated fatty acid activates but polyunsaturated fatty acid inhibits Toll-like receptor 2 dimerized with Toll-like receptor 6 or 1. J Biol Chem 279, 16971-16979.

Ley, R. E., Backhed, F., Turnbaugh, P., Lozupone, C. A., Knight, R. D., and Gordon, J. I. (2005). Obesity alters gut microbial ecology. Proc Natl Acad Sci USA 102, 11070-11075.

Ma, X., Hua, J., and Li, Z. (2008). Probiotics improve high fat diet-induced hepatic steatosis and insulin resistance by increasing hepatic NKT cells. J Hepatol 49, 821-830.

Maggard, M. A., Shugarman, L. R., Suttorp, M., Maglione, M., Sugerman, H. J., Livingston, E. H., Nguyen, N. T., Li, Z., Mojica, W. A., Hilton, L., Rhodes, S., Morton, S. C., and Shekelle, P. G. (2005). Meta-analysis: surgical treatment of obesity. Ann Intern Med 142, 547-559.

McKay, N. J., Kanoski, S. E., Hayes, M. R., and Daniels, D. (2011). Glucagon-like peptide-1 receptor agonists suppress water intake independent of effects on food intake. Am J Physiol Regul Integr Comp Physiol 301, R1755-1764.

Menani, J. V., and Johnson, A. K. (1998). Cholecystokinin actions in the parabrachial nucleus: effects on thirst and salt appetite. Am J Physiol 275, R1431-1437.

Menard, O., Gafa, V., Kapel, N., Rodriguez, B., Butel, M. J., and Waligora-Dupriet, A. J. (2010). Characterization of immunostimulatory CpG-rich sequences from different *Bifidobacterium* species. Appl Environ Microbiol 76, 2846-2855.

Mozaffarian, D., Hao, T., Rimm, E. B., Willett, W. C., and Hu, F. B. (2011). Changes in diet and lifestyle and long-term weight gain in women and men. N Engl J Med 364, 2392-2404.

Palazzo, M., Balsari, A., Rossini, A., Selleri, S., Calcaterra, C., Gariboldi, S., Zanobbio, L., Arnaboldi, F., Shirai, Y. F., Serrao, G., and Rumio, C. (2007). Activation of enteroendocrine cells via TLRs induces hormone, chemokine, and defensin secretion. J Immunol 178, 4296-4303.

Peterli, R., Steinert, R. E., Woelnerhanssen, B., Peters, T., Christoffel-Courtin, C., Gass, M., Kern, B., von Fluee, M., and Beglinger, C. (2012). Metabolic and hormonal changes after laparoscopic Roux-en-Y gastric bypass and sleeve gastrectomy: a randomized, prospective trial. Obes Surg 22, 740-748.

Rabot, S., Membrez, M., Bruneau, A., Gerard, P., Harach, T., Moser, M., Raymond, F., Mansourian, R., and Chou, C. J. (2010). Germ-free C57BL/6J mice are resistant to high-fat-diet-induced insulin resistance and have altered cholesterol metabolism. FASEB J 24, 4948-4959.

Schier, L. A., Davidson, T. L., and Powley, T. L. (2011). Ongoing ingestive behavior is rapidly suppressed by a preabsorptive, intestinal "bitter taste" cue. Am J Physiol Regul Integr Comp Physiol 301, R1557-1568.

Schlee, M., Wehkamp, J., Altenhoefer, A., Oelschlaeger, T. A., Stange, E. F., and Fellermann, K. (2007). Induction of human beta-defensin 2 by the probiotic *Escherichia coli* Nissle 1917 is mediated through flagellin. Infect Immun 75, 2399-2407.

Sloth, B., Davidsen, L., Hoist, J. J., Flint, A., and Astrup, A. (2007). Effect of subcutaneous injections of PYY1-36 and PYY3-36 on appetite, ad libitum energy intake, and plasma free fatty acid concentration in obese males. Am J Physiol Endocrinol Metab 293, E604-609.

Sturm, A., Rilling, K., Baumgart, D. C., Gargas, K., Abou-Ghazale, T., Raupach, B., Eckert, J., Schumann, R. R., Enders, C., Sonnenborn, U., Wiedenmann, B., and Dignass, A. U. (2005). *Escherichia coli* Nissle 1917 distinctively modulates T-cell cycling and expansion via toll-like receptor 2 signaling. Infect Immun 73, 1452-1465.

Teixeira, T. F., Collado, M. C., Ferreira, C. L., Bressan, J., and Peluzio Mdo, C. (2012). Potential mechanisms for the emerging link between obesity and increased intestinal permeability. Nutr Res 32, 637-647.

Troge, A., Scheppach, W., Schroeder, B. O., Rund, S. A., Heuner, K., Wehkamp, J., Stange, E. F., and Oelschlaeger, T. A. (2012). More than a marine propeller—the flagellum of the probiotic *Escherichia coli* strain Nissle 1917 is the major adhesin mediating binding to human mucus. Int J Med Microbiol 302, 304-314.

Turnbaugh, P. J., Ley, R. E., Mahowald, M. A., Magrini, V., Mardis, E. R., and Gordon, J. I. (2006). An obesity-associated gut microbiome with increased capacity for energy harvest. Nature 444, 1027-1031.

Ubeda, C., Lipuma, L., Gobourne, A., Viale, A., Leiner, I., Equinda, M., Khanin, R., and Pamer, E.G. (2012). Familial transmission rather than defective innate immunity shapes the distinct intestinal microbiota of TLR-deficient mice. J Exp Med 209, 1445-1456.

Verbalis, J. G., Richardson, D. W., and Stricker, E. M. (1987). Vasopressin release in response to nausea-producing agents and cholecystokinin in monkeys. Am J Physiol 252, R749-753.

Vijay-Kumar, M., Aitken, J. D., Carvalho, F. A., Cullender, T. C., Mwangi, S., Srinivasan, S., Sitaraman, S. V., Knight, R., Ley, R. E., and Gewirtz, A. T. (2010). Metabolic syndrome and altered gut microbiota in mice lacking Toll-like receptor 5. Science 328, 228-231.

Wang, H., Zhou, M., Brand, J., and Huang, L. (2009). Inflammation and taste disorders: mechanisms in taste buds. Ann N Y Acad Sci 1170, 596-603.

Wren, J. A., King, V. L., Campbell, S. L., and Hickman, M. A. (2007). Biologic activity of dirlotapide, a novel microsomal triglyceride transfer protein inhibitor, for weight loss in obese dogs. J Vet Pharmacol Ther 30 Suppl 1, 33-42.

Wu, S. V., Rozengurt, N., Yang, M., Young, S. H., Sinnett-Smith, J., and Rozengurt, E. (2002). Expression of bitter taste receptors of the T2R family in the gastrointestinal tract and enteroendocrine STC-1 cells. Proc Natl Acad Sci USA 99, 2392-2397.

Wu, X., Ballard, J., and Jiang, Y. W. (2005). Structure and biosynthesis of the BT peptide antibiotic from *Brevibacillus texasporus*. Appl Environ Microbiol 71, 8519-8530.

Zhong, Y., Huang, J., Tang, W., Chen, B., and Cai, W. (2012). Effects of probiotics, probiotic DNA and the CpG oligodeoxynucleotides on ovalbumin-sensitized Brown-Norway rats via TLR9/NF-kappaB pathway. FEMS Immunol Med Microbiol 66, 71-82.

Zhou, J., Martin, R. J., Tulley, R. T., Raggio, A. M., McCutcheon, K. L., Shen, L., Danna, S. C., Tripathy, S., Hegsted, M., and Keenan, M. J. (2008). Dietary resistant starch upregulates total GLP-1 and PYY in a sustained day-long manner through fermentation in rodents. Am J Physiol Endocrinol Metab 295, E1160-1166.

Zhou, J., Martin, R. J., Tulley, R. T., Raggio, A. M., Shen, L., Lissy, E., McCutcheon, K., and Keenan, M. J. (2009). Failure to ferment dietary resistant starch in specific mouse models of obesity results in no body fat loss. J Agric Food Chem 57, 8844-8851.

What is claimed is:

1. A pharmaceutical composition formulated for oral delivery, said pharmaceutical composition comprising isolated, purified BT lipopeptides set forth in SEQ ID NO: 1, SEQ ID NO: 2 and SEQ ID NO: 3, wherein the pharmaceutical composition is effective to induce body weight normalization and/or blood glucose normalization, wherein the isolated, purified BT lipopeptides are water soluble, and wherein the pharmaceutical composition is a chewing gum, a lozenge, or an oral spray, wherein the isolated, purified BT lipopeptides are present in the range of 100 to 100,000 mg per kg of the dry weight of the food consumed per day.

2. The pharmaceutical composition of claim 1, further comprising one or more isolated, purified BT lipopeptides set forth in SEQ ID NO:4, SEQ ID NO:5, SEQ ID NO:6, SEQ ID NO:7, SEQ ID NO:8, or SEQ ID NO:9.

3. The pharmaceutical composition of claim 1, further comprising isolated, purified BT lipopeptides set forth in SEQ ID NO: 4, SEQ ID NO: 5, SEQ ID NO: 6, SEQ ID NO: 7, SEQ ID NO: 8, and SEQ ID NO: 9.

4. The pharmaceutical composition of claim 1, wherein the isolated, purified BT lipopeptides are synthetic.

5. The pharmaceutical composition of claim 1, wherein the isolated, purified BT lipopeptides are isolated from *Brevibacillus texasporus*.

6. The pharmaceutical composition of claim 1, wherein the isolated, purified BT lipopeptides are provided in a single or divided dose.

* * * * *